(12) United States Patent
Weitz et al.

(10) Patent No.: US 12,296,045 B2
(45) Date of Patent: May 13, 2025

(54) COPOLYMERS FOR STABILIZING EMULSIONS AND/OR FORMING INTERFACIAL FILMS, AND METHODS THEREOF

(71) Applicant: President and Fellows of Harvard College, Cambridge, MA (US)

(72) Inventors: David A. Weitz, Cambridge, MA (US); Joerg G. Werner, Medford, MA (US); Julie V. Brouchon, Cambridge, MA (US); John Heyman, Cambridge, MA (US); Brendan Deveney, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 712 days.

(21) Appl. No.: 17/613,023

(22) PCT Filed: May 22, 2020

(86) PCT No.: PCT/US2020/034187
§ 371 (c)(1),
(2) Date: Nov. 19, 2021

(87) PCT Pub. No.: WO2020/242929
PCT Pub. Date: Dec. 3, 2020

(65) Prior Publication Data
US 2022/0241198 A1    Aug. 4, 2022

Related U.S. Application Data

(60) Provisional application No. 62/852,750, filed on May 24, 2019.

(51) Int. Cl.
| | |
|---|---|
| *A61K 9/107* | (2006.01) |
| *A61K 9/50* | (2006.01) |
| *C08F 220/14* | (2006.01) |
| *C08F 220/18* | (2006.01) |
| *C08F 220/24* | (2006.01) |
| *C08F 220/56* | (2006.01) |
| *C08F 230/06* | (2006.01) |

(52) U.S. Cl.
CPC ............ *A61K 9/107* (2013.01); *A61K 9/5026* (2013.01); *A61K 9/5089* (2013.01); *C08F 220/14* (2013.01); *C08F 220/1802* (2020.02); *C08F 220/1806* (2020.02); *C08F 220/24* (2013.01); *C08F 220/56* (2013.01); *C08F 230/06* (2013.01)

(58) Field of Classification Search
None
See application file for complete search history.

(56) References Cited

U.S. PATENT DOCUMENTS

| | | |
|---|---|---|
| 5,512,131 A | 4/1996 | Kumar et al. |
| 6,355,198 B1 | 3/2002 | Enoch et al. |
| 7,708,949 B2 | 5/2010 | Stone et al. |
| 8,765,485 B2 | 7/2014 | Link et al. |
| 9,038,919 B2 | 5/2015 | Link et al. |
| 9,039,273 B2 | 5/2015 | Weitz et al. |
| 2005/0172476 A1 | 8/2005 | Stone et al. |
| 2007/0003442 A1 | 1/2007 | Link et al. |
| 2015/0217246 A1 | 8/2015 | Holtze et al. |
| 2017/0209386 A1 | 7/2017 | Pagels et al. |
| 2018/0171373 A1 | 6/2018 | Weitz et al. |

FOREIGN PATENT DOCUMENTS

| | | |
|---|---|---|
| WO | WO 96/29629 A2 | 9/1996 |
| WO | WO 01/89787 A2 | 11/2001 |
| WO | WO 2004/002627 A2 | 1/2004 |
| WO | WO 2004/091763 A2 | 10/2004 |
| WO | WO 2005/021151 A1 | 3/2005 |
| WO | WO 2009/025802 A1 | 2/2009 |
| WO | WO 2010/151776 A2 | 12/2010 |
| WO | WO 2015/200616 A1 | 12/2015 |

OTHER PUBLICATIONS

Guo et al. (Soft Matter, 2016, 12, 9683-9691).*
International Search Report and Written Opinion mailed on Aug. 17, 2020, for Application No. PCT/US2020/034187.
International Preliminary Report on Patentability mailed on Dec. 2, 2021, for Application No. PCT/US2020/034187.

(Continued)

*Primary Examiner* — Patricia Duffy
*Assistant Examiner* — Garen Gotfredson
(74) *Attorney, Agent, or Firm* — Wolf, Greenfield & Sacks, P.C.

(57) ABSTRACT

The present invention generally relates to polymers and, in particular, to copolymers for stabilizing, e.g., emulsions or droplets. In certain aspects, the copolymers may comprise a relatively hydrophobic monomer and a relatively hydrophilic monomer polymerized together (e.g., randomly) to form the copolymer. Examples of hydrophobic monomers include methacrylates and vinylphenyls; examples of hydrophilic monomers include boronic acids or acid derivatives. Surprisingly, such random copolymers may act as surfactants, e.g., stabilizing droplets within the emulsion. In addition, in some cases, an interfacial film may be produced by exposing the copolymer to a complexing molecule, such as a polyol, that can complex with the copolymer to form the film. In some cases, the film may at least partially surround a droplet, and in certain embodiments, the film may be sufficiently sturdy such that the droplet can be removed from the emulsion. Other aspects include methods of making or using such copolymers (for example, for containing cells in droplets), kits involving such copolymers, or the like.

14 Claims, 21 Drawing Sheets

(56) References Cited

OTHER PUBLICATIONS

Guo et al., Dual responsive Pickering emulsions stabilized by constructed core crosslinked polymer nanoparticles via reversible covalent bonds. Soft Matter. Dec. 6, 2016;12(48):9683-9691. doi: 10.1039/c6sm02336c.
Kaji et al., Characterization of O/W Emulsions Prepared by PEG-Diisostearate Amphiphilic Random Copolymer. J Oleo Sci. Oct. 1, 2017;66(10):1121-1128. doi: 10.5650/jos.ess17044. Epub Sep. 15, 2017.
Lee et al., Fluorocarbon Oil Reinforced Triple Emulsion Drops. Adv Mater. Oct. 2016;28(38):8425-8430. doi: 10.1002/adma.201602804. Epub Aug. 1, 2016.
Peng et al., Anion amphiphilic random copolymers and their performance as stabilizers for O/W nanoemulsions. RSC Advances. May 10, 2019;9(26):14692-14700. doi: 10.1039/C9RA01383K.

\* cited by examiner $x : y = 99:1$ to $1:99$
$z_1 = 0-20; z_2 = 0-4$

FIG. 8A
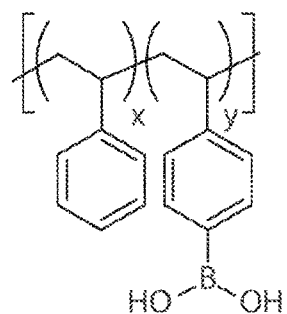
FIG. 8B
FIG. 9A
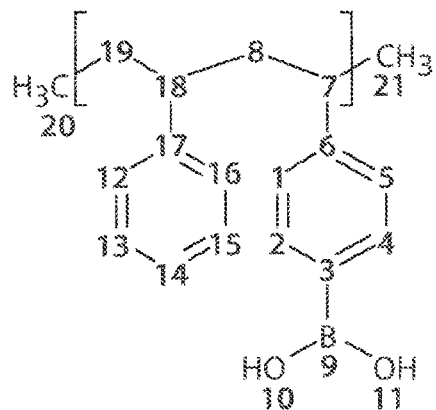
FIG. 9B

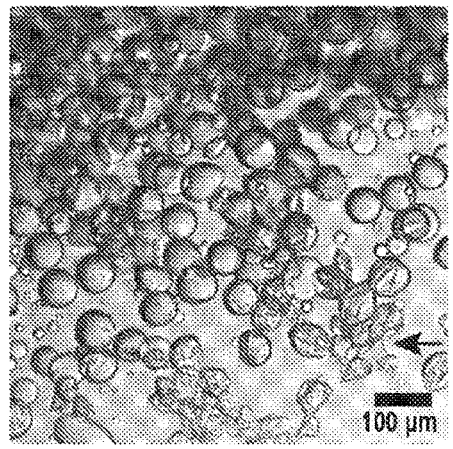 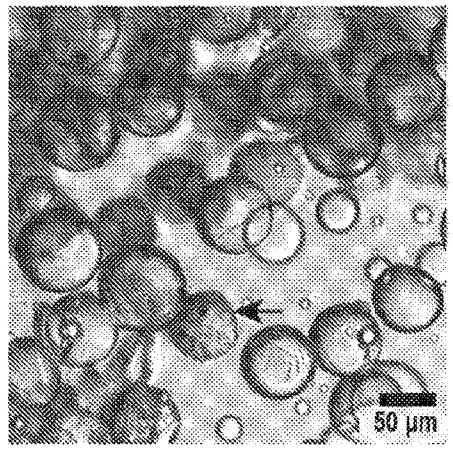
FIG. 10A  FIG. 10B
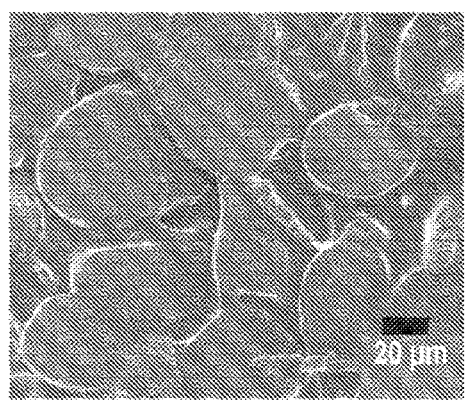 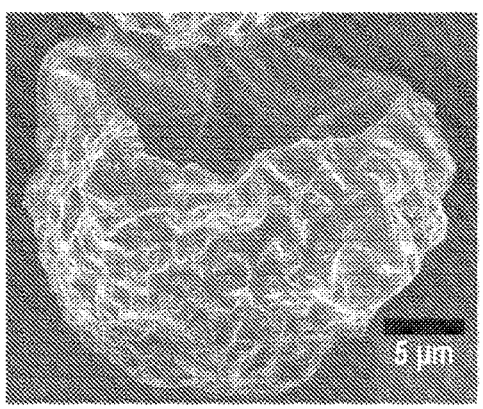
FIG. 10C  FIG. 10D
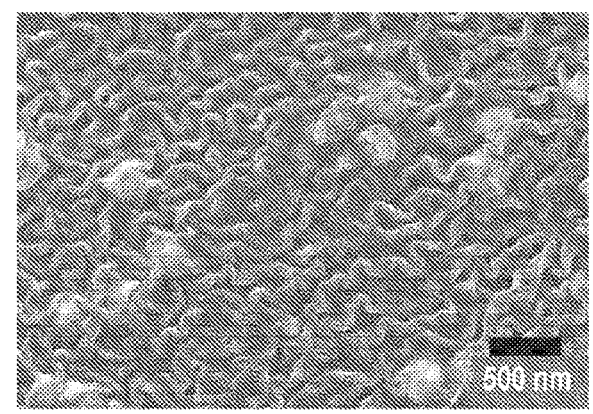
FIG. 10E

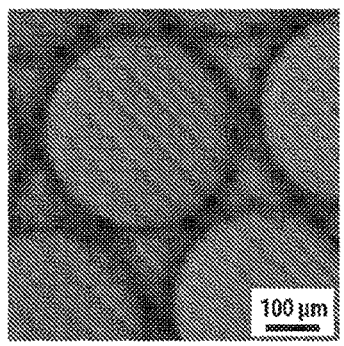 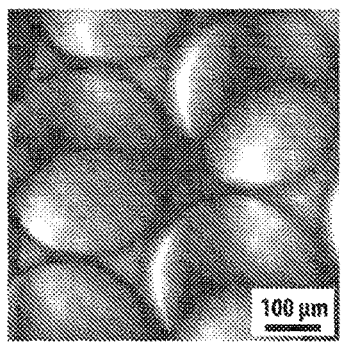 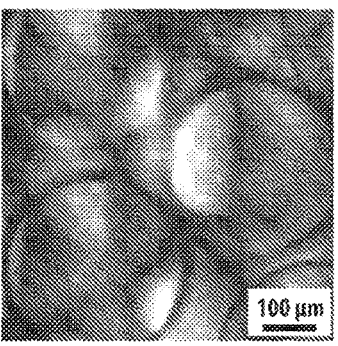
FIG. 16A　　　　FIG. 16B　　　　FIG. 16C
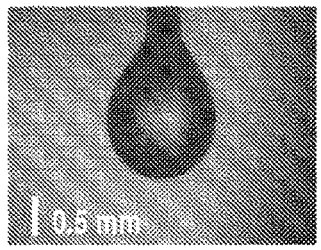 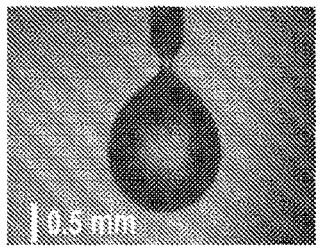 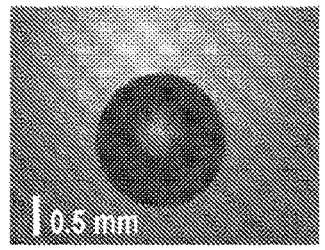
FIG. 17A　　　　FIG. 17B　　　　FIG. 17C

COPOLYMERS FOR STABILIZING EMULSIONS AND/OR FORMING INTERFACIAL FILMS, AND METHODS THEREOF

RELATED APPLICATIONS

This application is a U.S. National Stage Application claiming priority to International Application No. PCT/US2020/034187, filed May 22, 2020, by Weitz, et al. entitled "Copolymers for Stabilizing Emulsions and/or Forming Interfacial Films, and Methods Thereof," which claims the benefit of U.S. Provisional Patent Application Ser. No. 62/852,750, filed May 24, 2019, entitled "Copolymers for Stabilizing Emulsions and/or Forming Interfacial Films, and Methods Thereof," by Weitz, et al., each incorporated herein by reference in its entirety.

GOVERNMENT FUNDING

This invention was made with government support under Grant Nos. 1708729 and 1420570 awarded by the National Science Foundation, and under Grant No. EB023287 awarded by the National Institutes of Health. The government has certain rights in the invention.

FIELD

The present invention generally relates to polymers and, in particular, to copolymers for stabilizing, e.g., emulsions or droplets.

BACKGROUND

Emulsions are dispersions of at least two immiscible fluid phases. The typical structure of a two-fluid emulsion is one fluid phase dispersed in the second phase in the form of drops, where the second phase is continuous. In most immiscible liquid-liquid mixtures, the drops coalesce and the fluids separate over time into two completely demixed phases with the smallest interfacial area between them due to the interfacial energy that causes an energetic penalty. Typical examples of emulsions are oil drops dispersed in water (O/W) or the inverted architecture (W/O). Molecules and particles that are attracted to both fluid phases, for example, with hydrophilic and hydrophobic functionalities, may accumulate at the interface of the two immiscible fluids and may lower the interfacial energy. This can lead to a significant increase in the lifetime of the emulsions and often introduces a kinetic energy barrier to droplet coalescence, rendering the emulsions metastable. These emulsion-stabilizing molecules, so-called surfactants, typically contain a distinct hydrophobic part, the so-called hydrophobic tail, and a hydrophilic part, the so-called hydrophilic head group, in a small-molecule or polymeric architecture. Different forms of emulsions are used in many different products, applications, and industries, including food, medicine, paints, to name only a few.

An important property of water drop-based emulsions is droplet stability, i.e., the resistance to coalescence, as well as the molecular exchange between different droplets, which leads to cross-contamination. These may be facilitated with an interface-stabilizing surfactant. The surfactant may lower the interfacial energy of the water-hydrocarbon or water-fluorocarbon interface and provide a kinetic barrier to droplet coalescence. Common surfactants include small-molecule surfactants with hydrophobic or fluorinated alkyl chains and hydrophilic head groups, block copolymer type surfactants of A-B and A-B-A architecture with hydrophobic, or perfluorinated blocks A and a hydrophilic block B such as poly(ethylene glycol). However, despite the good stabilization capabilities of many of these surfactant systems, molecular exchange between aqueous drops and the associated contamination remains a major issue, especially in droplet-based biological assays using fluorinated oils as well as stability at extreme conditions such as elevated temperatures and bio-compatibility including single-cell compatibility.

SUMMARY

The present invention generally relates to polymers and, in particular, to copolymers for stabilizing, e.g., emulsions or droplets. The subject matter of the present disclosure involves, in some cases, interrelated products, alternative solutions to a particular problem, and/or a plurality of different uses of one or more systems and/or articles.

In one aspect, the present invention is generally directed to a composition. According to one set of embodiments, the composition comprises an aqueous fluid contained within an immiscible fluid. In some cases, the aqueous fluid and the immiscible fluid may form an interface stabilized with a random amphiphilic copolymer.

In another set of embodiments, the composition comprises an aqueous droplet encapsulated within a polymer film contained within an immiscible fluid. In certain embodiments, the polymer film comprises a complex of a random amphiphilic copolymer and a hydrophilic complexing molecule.

The present invention, in another set of embodiments, is directed to a method. In accordance with one set of embodiments, the method includes removing an aqueous droplet encapsulated in a polymeric film from an immiscible fluid. In certain instances, the polymer film comprises a complex of a random amphiphilic copolymer and a hydrophilic complexing molecule.

In another aspect, the present invention encompasses methods of making one or more of the embodiments described herein, for example, a copolymer as described herein. In still another aspect, the present invention encompasses methods of using one or more of the embodiments described herein, for example, a copolymer as described herein.

In another set of embodiments, the composition comprises an oil droplet encapsulated within a polymer film contained within an aqueous fluid. In certain embodiments, the polymer film comprises a complex of a random amphiphilic copolymer and a hydrophilic complexing molecule.

In another set of embodiments, the method comprises removing an oil droplet encapsulated in a polymeric film from an aqueous fluid. In certain embodiments, the polymer film comprises a complex of a random amphiphilic copolymer and a hydrophilic complexing molecule.

Other advantages and novel features of the present invention will become apparent from the following detailed description of various non-limiting embodiments of the invention when considered in conjunction with the accompanying figures.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 8A-8B are schematic diagrams illustrating a surfactant and a random copolymer;

FIGS. 9A-9C illustrates certain poly(styrene-co-4-vinylphenylboronic acid) copolymers, in yet another set of embodiments;

FIGS. 10A-10E illustrates certain aqueous droplets, in still another set of embodiments;

FIGS. 16A-16C illustrate confocal microscopy images of mammalian K562 cells expanding in water-in-fluorocarbon drops, in accordance with another set of embodiments; and FIGS. 17A-17C illustrate optical microscopy images of millimeter sized fluorocarbon-in-water emulsion drop formation (FIG. 17A and FIG. 17B) and fabricated drop (FIG. 17C), in accordance with another set of embodiments.

DETAILED DESCRIPTION

The present invention generally relates to polymers and, in particular, to copolymers for stabilizing, e.g., emulsions or droplets. In certain aspects, the copolymers may comprise a relatively hydrophobic monomer and a relatively hydrophilic monomer polymerized together (e.g., randomly) to form the copolymer. Examples of hydrophobic monomers include methacrylates and vinylphenyls; examples of hydrophilic monomers include boronic acids or acid derivatives. Surprisingly, such random copolymers may act as surfactants, e.g., stabilizing droplets within the emulsion. In addition, in some cases, an interfacial film may be produced by exposing the copolymer to a complexing molecule, such as a polyol, that can complex with the copolymer to form the film. In some cases, the film may at least partially surround a droplet, and in certain embodiments, the film may be sufficiently sturdy such that the droplet can be removed from the emulsion. Other aspects include methods of making or using such copolymers (for example, for containing cells in droplets), kits involving such copolymers, or the like.

It should be understood that a term such as "(meth) acrylate" suggests that both acrylates and methacrylates are possible in various embodiments. Similarly, a term such as "(meth)acrylamide" suggests that both acrylamides and methacrylamides are possible in various embodiments.

In one aspect, the present invention is generally directed to random copolymers that can be used as surfactants, for example, stabilizing droplets in an emulsion. Typically, an emulsion is formed from two immiscible fluids, such as a hydrophilic fluid (e.g., "water"), and a hydrophobic fluid (e.g., an "oil"), and a surfactant is used to stabilize droplets of one fluid in the other. A typical surfactant has a polar or "head" region that is attracted to the hydrophilic fluid, and a nonpolar or "tail" region that is attracted to the hydrophobic fluid. In such fashion, the surfactant typically can be found at the interface between the two fluids, and accordingly may stabilize droplets of one fluid in the other, e.g., as in an O/W emulsion (oil-in-water) or a W/O emulsion (water-in-oil).

However, although surfactants have been widely used for such purposes before, surprisingly, no one has previously suggested using a random copolymer as a surfactant. This may be because a random copolymer (e.g., having a random sequence of two or more different monomers) does not have an easily identifiable "head" (polar) and "tail" (nonpolar) characteristic of most surfactants. See, e.g., the example random copolymer in FIG. 8B. Instead, copolymers that have been used as surfactants are typically block copolymers that have relatively distinguishable polar and nonpolar regions.

Figure 1A:
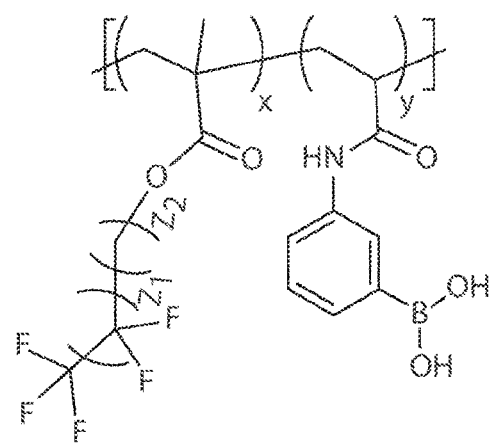
FIGS. 1A-1F illustrate certain copolymers and structures thereof, in accordance with one set of embodiments.

Accordingly, certain embodiments as discussed herein are directed to random copolymers that can be used as surfactants. One example of such a random copolymer is shown in FIG. 1A as a copolymer of a methacrylate (with x monomer units) and a boronic acid (with y monomer units). It should be understood that "x" and "y" are used to indicate the total number of monomer units within the random copolymer, but not the actual structure (i.e., a random copolymer may have x and y numbers of monomer units, but they are randomly distributed within the copolymer, rather than being all adjacent to each other as in a block copolymer).

In addition to stabilizing interfaces between fluids, e.g., fluidic droplets, in accordance with certain embodiments, random copolymers such as those discussed herein may be complexed with another complexing molecule, e.g., to form a polymer film at the interface.

For example, a polyol such as poly(vinyl alcohol) (PVA) may be complexed to the random copolymer, e.g., to the boronic acid units within the copolymer, which may result in the formation of a polymeric complex or network via boronic ester bonds. In some embodiments, such polymer films may be relatively sturdy, and in certain cases, sufficient to allow fluidic droplets to be removed or separated from the solution.

The above discussion is a non-limiting example of one embodiment of the present invention that is generally directed to a random copolymer. However, other embodiments are also possible. Accordingly, more generally, various aspects of the invention are directed to various systems and methods for polymers and, in particular, to copolymers for stabilizing, e.g., emulsions or droplets.

In one aspect, the present invention is generally directed to random copolymers comprising a first monomer and a second monomer that are polymerized together to form the final copolymer. The first monomer may be relatively hydrophilic and the second monomer may be relatively hydrophobic. These may be determined, for example, relative to each other. In addition, an amphiphilic copolymer is a copolymer that has both relatively hydrophilic monomers and relatively hydrophobic monomers.

In addition, in some embodiments, the first monomer may be a hydrophilic monomer, and the second monomer may be a hydrophobic monomer. Hydrophilicity/hydrophobicity may be determined, for example, by forming polymers consisting only of one monomer, and determining the water contact angle. Hydrophobic polymers may exhibit a contact angle of less than 90°, while hydrophilic polymers may exhibit a contact angle of greater than 90°.

In a random copolymer, the units forming the polymer are randomly distributed. Typically, a copolymer will be formed of two types of monomer units, although in some cases, there may be 3, 4, 5, or more types of monomer units present within the copolymer. As known by those of ordinary skill in the art, in a random copolymer, the monomers are randomly or statistically distributed along the chain and can include single monomers or larger blocks. However, the probability of finding a given monomer within any location within the polymer chain will depend largely on the relatively proportion of that monomer within the overall distribution of monomers, and is mostly independent of sequence position. In contrast, other types of copolymers, such as block copolymers, do not exhibit such a probabilistic distribution of monomers within the overall copolymer.

In certain embodiments, the random copolymer may be used as a surfactant, e.g., to stabilize the interface between two fluids, which are typically immiscible with each other. For example, one fluid may be a hydrophilic fluid while the other may be a hydrophobic fluid.

Examples of aqueous or hydrophilic liquids include, but are not limited to, water and other aqueous solutions comprising water, such as cell or biological media, cell culture media, biological buffers (e.g., phosphate buffered saline), cell lysis buffer, aqueous or hydrophilic liquid(s) comprising one or more PCR reagents, aqueous or hydrophilic liquid(s) comprising one or more RT-PCR reagents, biological assays, cell-cell interaction assays, detection assays including detecting antibodies, aqueous or hydrophilic liquid(s) comprising one or more biological entity (e.g., virus particle or mammalian cell, bacterial cell, fungal cell, etc.), ethanol, salt solutions, etc. Other examples include, but are not limited to, alcohols (e.g., butanol (for example, tert-butanol), isopropanol (IPA), propanol (e.g., n-propanol), methanol, glycerin, or the like), blood, acids (e.g., formic acid, acetic acid, or the like), amines (e.g., dimethyl amine, diethyl amine, or the like), dimethyl sulfoxide (DMSO), acetonitrile (MeCN), dimethylformamide (DMF), acetone, mixtures of these, and/or other similar fluids.

Examples of hydrophobic liquids include, but are not limited to, oils such as hydrocarbons, silicon oils, fluorocarbon oils, fluorinated oils, organic solvents etc. In some cases, the hydrophobic liquid comprises a fluorinated oil and/or a hydrocarbon oil. Non-limiting examples include methoxyperfluorobutane, HFE-7500 3M™ Novec™ engineered fluid, HFE-7100 3M™ Novec™ engineered fluid, or 3M™ Fluorinert™ Electronic Liquid FC-40, hexafluorobenzene, tetradecafluorohexane, or other perfluoroalkanes. Non-limiting examples of hydrocarbons include benzene, toluene, hexane, hexadecane, or other alkanes, chloroform, dichloromethane, or other halogenated alkanes, diethyl ether, or other alkyl ethers, ethyl acetate, alkyl acetates, or other alkyl carboxylates, n-butanol, 1-octanol, or other aliphatic alcohols. In some cases, the fluorinated oil may have structures such as:

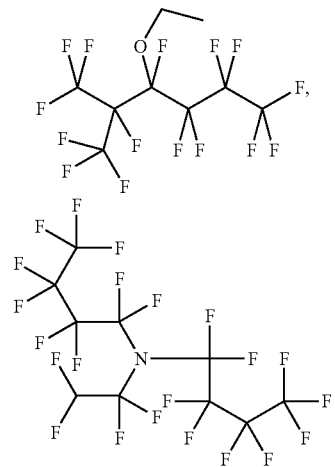

Those of ordinary skill in the art will often refer to these as the "water" and "oil" phase, respectively, of the emulsion, as in an oil/water ("O/W") emulsion (i.e., with discrete droplets of hydrophobic fluid in a continuous hydrophilic fluid) or a water/oil ("W/O") emulsion (i.e., with discrete droplets of hydrophilic fluid in a continuous hydrophobic fluid). However, it will be understood that such terminology is not intended to be limited to only pure water and pure oil emulsions, but also includes more generally emulsion systems from relatively immiscible mixtures of suitable hydrophilic liquids ("W") and hydrophobic liquids ("O"), including any of the ones described herein.

Without wishing to be bound by any particular theory, in certain embodiments, hydrophobic liquid (e.g., oil)-soluble boronic acid copolymers generally reduce the interfacial tension between hydrophilic liquids (e.g., water) and hydrophobic liquids (e.g., oil). The interfacial tension may be further reduced when one or more complexing molecules are added to the hydrophilic phase (e.g., water). As a non-limiting example, an interfacial tension of HFE-7500 and aqueous cell culture medium (Dulbecco's Modified Eagle Medium, DMEM) was measured using a pendant drop to be 30.9 milliNewtons/meter (mN/m). An interfacial tension between a solution of 3 wt % poly(1H,1H,2H,2H-perfluorodecyl(meth)acrylate-co-3-(acrylamido)phenylboronic acid) (PFDMA-APBA) in HFE-7500 and DMEM was measured to be 24.3 mN/m. An interfacial tension between a solution of 3 wt % PFDMA-APPA in HFE-7500 and a solution of 2 wt % PVA in DMEM was measured to be 9.2 mN/m. An interfacial tension between HFE-7500 and a solution of 2 wt % PVA in DMEM was measured to be 11.7 mN/m. An interfacial tension between a solution of 3 wt PFDMA-APBA in HFE-7500 and deionized water was measured to be 21.4 mN/m.

Typically, two fluids that are immiscible will separate if left undisturbed under ambient conditions to form a system where a first fluid is substantially layered on top of a second fluid. For example, if the first fluid and the second fluid are mixed together, one may form droplets within the other fluid, but the droplets will separate (e.g., due to differences in fluid density) and coalesce to form a layer of fluid. Those of ordinary skill in the art will understand that "miscibility" does not imply that the miscibility must be perfect, i.e., some molecules of one fluid may be found within the other, resulting in some degree of mixing, even after the bulk of the fluids have separated, e.g., forming different layers.

In contrast, however, if a surfactant is present, then such phase-separation of the droplets into distinct layers may not occur, at least for reasonable periods of time. Instead, the system may be stable, e.g., the surfactants allow one fluid to stably remain as separate, discrete droplets distributed within the other fluid for indefinite periods of time.

As noted above, in one set of embodiments, the surfactant may be a random copolymer. Surprisingly, certain types of random copolymers may be able to act as surfactants to stabilize two immiscible fluids as an emulsion, despite the lack of any readily distinct "head" (hydrophilic) and "tail" (hydrophobic) portions within the random copolymer. Instead, in a random copolymer, the monomers forming the copolymer may be relatively hydrophilic and relatively hydrophobic, but there is no apparent spatially separable portions of each, as the monomers are randomly distributed within the copolymer. However, such random copolymers can nonetheless act as surfactants to stabilize the two fluids, e.g., to form an emulsion of droplets.

It should also be understood that in some embodiments, other surfactants may be present, e.g., in addition to the ones described above. Examples of surfactants include, but are not limited to, sodium dodecyl sulfate (SDS), ammonium lauryl sulfate, sodium lauryl sulfate, sodium laureth sulfate, dioctyl sodium sulfosuccinate, perfluorooctanesulfonate (PFOS), perfluorobutanesulfonate, alkyl aryl ether phosphate, alkyl ether phosphate, alkyl carboxylates, fatty acid salts (soaps), sodium stearate, sodium lauroyl sarcosinate, carboxylate fluorosurfactants, perfluorononanoate, perfluorooctanoate (PFOA or PFO), cetyl trimethylammonium bromide (CTAB), hexadecyl trimethyl ammonium bromide, cetyl trimethylammonium chloride (CTAC), cetylpyridiniumchloride (CPC), polyethoxylated tallow amine (POEA), benzalkonium chloride (BAC), benzethonium chloride (BZT), or the like.

In certain embodiments, the copolymer may include a relatively hydrophilic monomer. In one set of embodiments, for example, the relatively hydrophilic monomer may comprise a boronic acid. Boronic acids typically have a structure *—B(OH)$_2$, where * indicates a point of attachment. Examples of boronic acids include, but are not limited to, phenylboronic acid, alkylboronic acids such as methylboronic acid, ethylboronic acid, etc., alkenylboronic acids such as propenylboronic acid, butenylboronic acid, etc., or the like. In another set of embodiments, the relatively hydrophilic monomer may comprise another acid, including but not limited to carboxylic acids or a sulfonic acids. In some sets of embodiments, the relatively hydrophilic monomer may comprise an activated form of an acid such as but not limited to acid chlorides, acid esters, for example phenylboronic acid ethylene glycol ester. Without wishing to be bound by any theory, it is believed that boronic acids can form bonds with diols and/or polyols quickly and efficiently. However, other acids would also work, as well as acid derivatives that react with alcohols or amines such as acid chlorides or activated esters, for example, having protection groups, e.g., that can be easily removed in some cases. In one set of embodiments, a monomer may be N-[3-(4,4,5,5-tetramethyl-1,3,2-dioxaborolan-2-yl)phenyl] acrylamide (CAS RN 874363-18-5). In these cases, in certain embodiments (e.g., after polymerization), a deprotection step may be carried out to remove the pinacol and activate the boronic acid and its surfactant functionality.

In one set of embodiments, a monomer unit including the boronic acid may be based on a methacrylamide structure, such as a methyl methacrylamide structure. As a non-limiting example, the boronic acid may be a phenylboronic acid, attached to a methacrylamide structure to form a 3-(acrylamido)phenylboronic acid, e.g., as in the structure:

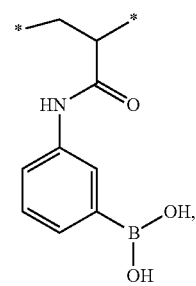 [SMILES: *CC(*)C(=O)Nc1cccc(B(O)O)c1]

wherein * indicates attachment to the polymer backbone.

The copolymer may also include a relatively hydrophobic monomer. For example, the relatively hydrophobic monomer may comprise a (meth)acrylate, including methacrylates such as a methyl methacrylate, or acrylates such as hexyl acrylate. The monomer may also comprise vinylphenyls such as styrene, alkenes such as propene, or dienes such as butadiene or isoprene. A typical methacrylate may have a monomer repeat unit, such as:

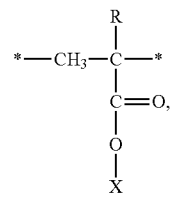

where X varies depending on the type of acrylate, R may be —H or an alkyl, such as methyl, ethyl, propyl, butyl, pentyl, hexyl, etc., and * indicates attachment to the polymer backbone. In addition, the alkyl may be substituted or unsubstituted. The alkyl may also be branched or unbranched. In one embodiment, the alkyl is a straight-chain unsubstituted alkyl, for example, having 1, 2, 3, 4, 5, 6, 7, 8, 9, or 10 carbons.

In some embodiments, X may be a perfluoroalkyl, i.e., having a structure —$(CF_2)_a$—$CF_3$, where a is 0 or a positive integer. For example, "a" of —$(CF_2)_a$—$CF_3$ may be 1, 2, 3, 4, 5, 6, 7, 8, 9, 10, 11, 12, 13, 14, 15, 16, 17, 18, 19, 20, or more. In addition in some cases, X may be a perfluoroalkyl alkyl methacrylate, e.g., having a structure —$(CH_2)_b$—$(CF_2)_a$—$CF_3$, i.e., where the perfluoroalkyl group is attached to another alkyl —(CH$_2$)$_b$— group. b may be 0 or a positive integer, e.g., b may be 1, 2, 3, 4, 5, 6, 7, 8, 9, 10, etc. In some cases, the alkyl may be a straight-chain unsubstituted alkyl, e.g., having a formula —(CH$_2$)$_b$—, although in other cases, the alkyl may comprise 1, 2, 3, or more substituents, and/or the alkyl may be a branched alkyl. Without wishing to be bound by any theory, perfluoroalkyls may be used to facilitate polymer solubility in hydrophobic liquids or oils.

Thus, for example, the monomer may have a structure *—C(=O)—O—(CH$_2$)$_a$—(CF$_2$)$_b$—CF$_3$, where * indicates a point of attachment, x is 0 or a positive integer, and y is 0 or a positive integer. In some cases, the monomer may have a structure:

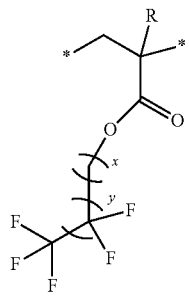

where R is —H or an alkyl (for example, methyl, ethyl, etc.), * indicates attachment to the polymer backbone, x is 0 or a positive integer, and y is 0 or a positive integer. Non-limiting examples of such monomers include 1H,1H,2H,2H-perfluorodecyl methacrylate, 2,2,3,3,4,4,4-heptafluorobutyl methacrylate, or hexylacrylate. Another non-limiting example of such a monomer is 1H,1H,2H,2H-heptadecafluorodecyl acrylate (GAS 27905-45-9).

The monomers may be present within the copolymer in any suitable ratio. For example, if the copolymer has only two monomers, the monomers may be present in monomeric ratios of as low as 1:999 up to 1:1, at least a 1:99 ratio, at least a 5:95 ratio, at least a 10:90 ratio, at least a 20:80 ratio, at least a 30:70 ratio, at least a 40:60 ratio, at least a 50:50 ratio, at least a 60:40 ratio, at least a 70:30 ratio, at least a 80:20 ratio, at least a 90:10 ratio, at least a 95:5 ratio, or at least a 99:1 (by mole). The monomers may also be present in no more than a 99:1 ratio, no more than a 95:5 ratio, no more than a 90:10 ratio, no more than a 80:20 ratio, no more than a 70:30 ratio, no more than a 60:40 ratio, no more than a 50:50 ratio, no more than a 40:60 ratio, no more than a 30:70 ratio, no more than a 20:80 ratio, no more than a 10:90 ratio, no more than a 5:95 ratio, or no more than a 1:99 ratio. Combinations of any of these are also possible, e.g., the monomers may be present in a ratio between 10:90 and 30:70.

In certain embodiments, random copolymers of one or more hydrophobic (meth)acrylate or (meth)acrylamide copolymerized with one or more hydrophilic (meth)acrylate or (meth)acrylamide in a random copolymer architecture are provided. One such copolymer is shown in FIG. 1A. Some non-limiting examples of such copolymers include poly(1H, 1H,2H,2H-perfluorodecyl(meth)acrylate-co-3-(acrylamido) phenylboronic acid), herein further abbreviated as PFDMA-APBA; poly(2,2,3,3,4,4,4-heptafluorobutyl methacrylate-co-3-(acrylamido)phenylboronic acid), herein further abbreviated as PFBMA-APBA; poly(ethylmethacrylate-co-3-(acrylamido)phenylboronic acid), herein further abbreviated as PEMA-APBA; PFDA-APBA, obtained from the monomers 1H,1H,2H,2H-heptadecafluorodecyl acrylate and 3-(acrylamido)phenyl boronic acid; and poly(hexylacrylate-co-3-(acrylamido)phenylboronic acid), herein abbreviated as PHA-APBA, and poly(styrene-co-4-vinylphenylboronic acid), herein abbreviated as PS-VPBA. The (meth) and (M) addition describes the possibility of using either acrylic or methacrylic monomers of the same pendant side groups.

The copolymer may also have any suitable size or molecular weight. For instance, the molecular weight (weight average) may be at least 1 kDa, at least 2 kDa, at least 3 kDa, at least 5 kDa, at least 7 kDa, at least 10 kDa, at least 20 kDa, at least 30 kDa, at least 50 kDa, at least 70 kDa, at least 100 kDa, at least 200 kDa, at least 300 kDa, at least 500 kDa, etc. In addition, in some cases, the molecular weight may be no more than 500 kDa, no more than 300 kDa, no more than 200 kDa, no more than 100 kDa, no more than 70 kDa, no more than 50 kDa, no more than 30 kDa, no more than 20 kDa, no more than 10 kDa, no more than 7 kDa, no more than 5 kDa, no more than 3 kDa, no more than 2 kDa, no more than 1 kDa, etc. Combinations of any of these are also possible, e.g., the molecular weight may be between 1 kDa and 3 kDa.

In some embodiments, a complexing molecule may be present. In some cases, the complexing molecule may initially be present in the aqueous phase. The complexing molecule may interact with the random copolymer to form a polymeric film. For instance, the complexing molecule may cross-link with the random copolymer via boronic ester bonds between boronic acid groups on the random copolymer and hydroxide groups on the complexing molecule. Thus, for example, the complexing molecule may be rich in hydroxide groups that can interact with groups on the random copolymer. Non-limiting examples of such complexing molecules with hydroxide groups include 1,2- and 1,3-diols (see, e.g., FIG. 1B) and polyols such as glucose. 1,2-diols, sometimes also referred to as alpha-diols, are molecules that possess at least 2 hydroxyl (—OH) groups at adjacent carbons in the molecule, such as in ethylene glycol. 1,3-diols, sometimes also referred to as beta-diols, are molecules that possess at least 2 hydroxyl (—OH) groups two carbons apart in the molecule, such as in propylene glycol. Other non-limiting examples include monosaccharides, disaccharides, polysaccharides, or glycoproteins (carbohydrate/sugar-containing proteins) or molecules and polymers containing multiple catechol units or 1,2- and 1,3-hydroxy functionalities such as polyvinyl alcohol or iodixanol, a radiocontrast agent and contained in the common density gradient medium OptiPrep™. If the complexing molecule is a larger molecule or polymer, then in some cases the repeat units of the polymer may include one or more hydroxide groups, or one or more 1,2- and/or 1,3-diols. For example, in one set of embodiments, the complexing molecule is a polyol, such as polyvinyl alcohol (PVA). The polymer may have any suitable molecular weight. For instance, the molecular weight (weight average) may be at least 1 kDa, at least 2 kDa, at least 3 kDa, at least 5 kDa, at least 7 kDa, at least 10 kDa, at least 20 kDa, at least 30 kDa, at least 50 kDa, at least 100 kDa, at least 200 kDa, at least 300 kDa, at least 500 kDa, at least 1,000 kDa, at least 2,000 kDa, etc. In addition, in some cases, the molecular weight may be no more than 10 kDa, no more than 7 kDa, no more than 5 kDa, no more than 3 kDa, no more than 2 kDa, no more than 1 kDa, etc. Combinations of any of these are also possible, e.g., the molecular weight may be between 1 kDa and 3 kDa. For example, in another set of embodiments, the complexing molecule contains multiple 1,2-diols such as iodixanol, cyclodextrin, or the like. Ioodixanol has the chemical name 5-[acetyl-[3-[acetyl-[3,5-bis(2,3-dihydroxypropylcarbamoyl)-2,4,6-triiodo-phenyl]amino]-2-hydroxypropyl]amino]-N,N'-bis(2,3-dihydroxypropyl)-2,4,6-triiodo-benzene-1,3-dicarboxamide). Some non-limiting examples of complexing molecules include proteins, such as those contained in fetal bovine serum (FBS) (e.g., components of FBS), bovine serum albumin (BSA), and glycated proteins and glycoproteins, as well as glycolipids.

In some cases, the complexes can be reversed. For example, the pH may be lowered, which may remove the cross-links in the polymer film. In some cases, the complexes can be reversed through the addition of a competing species, for instance, a competing diol such as ethylene glycol, glucose, or catechol, e.g., due to the high chemical reversibility of the boronic ester formation reaction.

In certain aspects, the complexing molecule may interact with the random copolymer to form a polymeric structure, such as a film. For example, if the random copolymer is present at an interface between two fluids, the addition of the complexing molecule may cause the interface to become at least partially solid, e.g., forming a film at the interface between the fluids. The film may be, for example, present at the interface between two layers of fluid, or if one fluid is present as droplets in a second fluid, the film may partially or fully encapsulate the droplets of the first fluid within the second fluid.

In some cases, such a film may be sufficiently stable such that it is a solid. For example, if a fluid is present as droplets within an emulsion, the film may be sufficiently solid that the fluid is encapsulated in the polymer. In some embodiments, the polymer may be sufficiently stable that it can be removed from the emulsion, e.g., as a capsule containing the fluidic droplet. The capsule can be removed from the emulsion by any suitable technique, for instance, by hand, mechanically (e.g., using a filter), or with electric or magnetic fields, or the like.

After removal, the capsule can then be manipulated by any other techniques, for instance, by adding it to another liquid, by removing the capsule (for example, using a change in pH or adding a competitive species, as discussed above), or the like.

In some embodiments, the polymer film is relatively thin. The use of thin films can provide a number of advantages. For example, the film can dissolve relatively quickly in some cases. In some embodiments, this may allow a particle to deliver its contents prior to being transported away from the target medium.

In some embodiments, the film has an average thickness (averaged over the entire droplet) of less than about 0.05, less than about 0.01, less than about 0.005, or less than about 0.001 times the average cross-sectional diameter of the droplet, or between about 0.0005 and about 0.05, between about 0.0005 and about 0.01, between about 0.0005 and about 0.005, or between about 0.0005 and about 0.001 times the average cross-sectional diameter of the droplet. In some embodiments, the film has an average thickness of less than about 10 micrometers, less than about 5 micrometers, less than about 1 micron, less than about 500 nm, or less than about 100 nm, or between about 50 nm and about 1 micron, between about 50 nm and about 500 nm, or between about 50 nm and about 100 nm. In some embodiments, at least about 50%, at least about 75%, at least about 90%, at least about 95%, or at least about 99% of the droplets in an emulsion includes a film having an average thickness within any of the ranges outlined in this paragraph. One of ordinary skill in the art would be capable of determining the average thickness of a film by, for example, examining scanning electron microscope (SEM) images of the droplets.

The droplets within the emulsion (or capsules formed encapsulating such droplets) may have any suitable size or size distribution. The droplets may be monodisperse, or be present in a range of sizes or diameters. For example, the average diameter of the droplets may be less than about 1 cm, less than about 5 mm, less than about 3 mm, less than about 2 mm, less than about 1 mm, less than about 500 micrometers, less than about 300 micrometers, less than about 200 micrometers, less than about 100 micrometers, less than about 75 micrometers, less than about 50 micrometers, less than about 30 micrometers, less than about 25 micrometers, less than about 20 micrometers, less than about 15 micrometers, less than about 10 micrometers, less than about 5 micrometers, less than about 3 micrometers, less than about 2 micrometers, less than about 1 micrometer, less than about 500 nm, less than about 300 nm, less than about 100 nm, or less than about 50 nm. The average diameter of the droplet may also be at least about 30 nm, at least about 50 nm, at least about 100 nm, at least about 300 nm, at least about 500 nm, at least about 1 micrometer, at least about 2 micrometers, at least about 3 micrometers, at least about 5 micrometers, at least about 10 micrometers, at least about 15 micrometers, or at least about 20 micrometers in certain cases. Combinations of these are also possible, e.g., the droplet may have an average diameter of between about 25 micrometers and about 100 micrometers. In certain embodiments, droplets (e.g., oil droplets) have an average diameter of below 3 mm, e.g., below 1 mm, between or equal to 1 micron and 5 microns. The average diameter of the droplets may be taken as the arithmetic average of the droplets in the emulsion. For droplets that are non-spherical, the diameter of the droplet may be taken as the diameter of a perfect sphere having the same volume as the droplet. Those of ordinary skill in the art will be familiar with techniques for producing emulsions and droplets such as microfluidic droplets; see, for example, Int. Pat. Apl. Pub. Nos. WO 2004/002627, WO 2004/091763, or WO 2005/021151, each incorporated herein by reference in its entirety.

In some embodiments, the droplets have an overall average diameter and a distribution of diameters such that no more than about 5%, no more than about 2%, or no more than about 1% of the droplets have a diameter less than about 90% (or less than about 95%, or less than about 99%) and/or greater than about 110% (or greater than about 105%, or greater than about 101%) of the overall average diameter of the droplets.

In some embodiments, the droplets have an overall average diameter and a distribution of diameters such that the coefficient of variation of the cross-sectional diameters of the droplets is less than about 10%, less than about 5%, less than about 2%, between about 1% and about 10%, between about 1% and about 5%, or between about 1% and about 2%. The coefficient of variation can be determined by those of ordinary skill in the art, and may be defined as:

$$c_v = \frac{\sigma}{|\mu|} \qquad [1]$$

wherein $\sigma$ is the standard deviation and $\mu$ is the mean.

Those of ordinary skill in the art will be familiar with systems and methods of creating droplets and emulsions. In some cases, an emulsion may be formed by mixing two fluids together and disrupting the mixture to form droplets (e.g., during and/or after the fluids are mixed together), for example mechanically (e.g., by shaking). In certain embodiments, an emulsion can be prepared by creating a plurality of droplets of a first fluid in a second fluid, for example, using microfluidic techniques. Those of ordinary skill in the art will be familiar with techniques for forming droplets and/or emulsions. See, e.g., U.S. Pat. Nos. 7,708,949, 8,765, 485, 9,038,919, or 9,039,273, each incorporated herein by reference. Additional examples of the production of droplets of fluid surrounded by a liquid or carrying fluid are described in International Patent Application Serial No. PCT/US2004/ 010903, filed Apr. 9, 2004 by Link, et al. and International Patent Application Serial No. PCT/US03/20542, filed Jun. 30, 2003 by Stone, et al., published as WO 2004/002627 on Jan. 8, 2004, each incorporated herein by reference.

In some cases, the droplets within the emulsion may also contain one or more species. For example, one or more droplets may contain a cell, or more than one cell, e.g., multiple cells, two or more interacting cells (e.g., immune cells, cancer cells). Non-limiting examples of cells include T cells and/or Antigen Presenting Cells, and/or stem cells. Other examples include, but are not limited to, cell spheroids or cells aggregates (e.g., tumor spheroids, stem cell spheroids), or other 3D tissue structures, such as organoids, and/or colonies. In some cases, these may have dimensions of at least 1 micrometer, 10 micrometers, 100 micrometers, or several hundred micrometers.

As other non-limiting examples, the droplets may contain a species such as a chemical, biochemical, or biological entity, one or more viruses, one or more bacteria, a particle, a bead, gases, molecules, a pharmaceutical agent, a drug, polynucleotides (e.g., DNA, RNA), DNA, RNA, proteins, a fragrance, a reactive agent, a biocide, a fungicide, a pesticide, a preservative, or the like. Additional non-limiting examples of species that may be present include, for example, biochemical species such as nucleic acids such as siRNA, RNAi and DNA, proteins, peptides, or enzymes. Still other examples of species include, but are not limited to, nanoparticles, quantum dots, fragrances, proteins, indicators, dyes, fluorescent species, chemicals, or the like. Non-limiting examples of fluorescent species and/or dyes include fluorescein sodium salt, Rhodamine 6(1. EvaGreen™, CellTracker™ Green CMFDA Dye, Sytox red, sulforhodamine B. As yet another example, the species may be a drug, a pharmaceutical agent, or other species that has a physiological effect when ingested or otherwise introduced into the body, e.g., to treat a disease, relieve a symptom, or the like. In some embodiments, the drug may be a small-molecule drug, e.g., having a molecular weight of less than about 2000 Da, less than about 1500 Da, less than about 1000 Da, or less than about 500 Da.

If a cell is present, the cell may be any suitable cell. The cell may be for example, from a specific population of cells, such as from a certain organ or tissue (e.g., cardiac cells, immune cells, muscle cells, cancer cells, tumor cells, etc.), cells from a specific individual or species (e.g., human cells, mammalian cells, mouse cells, bacteria, etc.), cells from different organisms, cells from a naturally-occurring sample (e.g., pond water, soil, etc.), or the like. In some cases, the cells may be dissociated from tissue.

In another set of embodiments, the composition comprises an oil droplet encapsulated within a polymer film contained within an aqueous fluid. In certain embodiments, the polymer film comprises a complex of a random amphiphilic copolymer and a hydrophilic complexing molecule. In some embodiments, the oil droplet comprises a hydrocarbon and/or a fluorocarbon. In some embodiments, the hydrophilic complexing molecule comprises a hydrophilic polyol (e.g., polyvinyl alcohol (PVA)). In some embodiments, the random amphiphilic copolymer comprises a lipophilic boronic acid copolymer (e.g., poly(hexylacrylate-co-3-(acrylamido)phenylboronic acid) (PHA-APBA)). In some embodiments, the random amphiphilic copolymer comprises a fluorophilic boronic acid copolymer (e.g., PFDA-APBA, obtained from the monomers 1H,1H,2H,2H-heptadecafluorodecyl acrylate and 3-(acrylamido)phenyl boronic acid). In some embodiments, the random amphiphilic copolymer comprises poly(1H,1H,2H,2H-perfluorodecyl(meth) acrylate-co-3-(acrylamido)phenylboronic acid) (PFDMA-APBA). In some embodiments, the aqueous fluid comprises Dulbecco's Modified Eagle Medium (DMEM). In some embodiments, the oil droplet has a diameter below 3 mm (e.g., below 1 mm, from 1 micron to 5 microns).

In another set of embodiments, the method comprises removing an oil droplet encapsulated in a polymeric film from an aqueous fluid. In certain embodiments, the polymer film comprises a complex of a random amphiphilic copolymer and a hydrophilic complexing molecule. In some cases, the method comprises adding the encapsulated oil droplet to a second fluid. The aqueous fluid may comprise, for example, cell or biological media. In some embodiments, the method may also comprise growing cells on the surface of the encapsulated oil droplet in the aqueous fluid. In certain cases, the second fluid is a non-aqueous fluid.

The following are incorporated herein by reference: U.S. Provisional Patent Application Ser. No. 62/852,750, filed May 24, 2019, entitled "Copolymers for Stabilizing Emulsions and/or Forming Interfacial Films, and Methods Thereof," by Weitz, et al.; Int. Pat. Apl. Pub. No. WO 2010/151776, filed Jun. 25, 2010, entitled "Fluid Injection," by Weitz, et al.; and Int. Pat. Apl. Pub. No. WO 2015/ 200616, filed Jun. 25, 2015, entitled "Fluid Injection Using Acoustic Waves," by Weitz, et al. In addition, the following documents are incorporated herein by reference: U.S. patent application Ser. No. 11/360,845, filed Feb. 23, 2006, entitled "Electronic Control of Fluidic Species," by Link, et al., published as U.S. Patent Application Publication No. 2007/ 0003442 on Jan. 4, 2007; U.S. patent application Ser. No. 08/131,841, filed Oct. 4, 1993, entitled "Formation of Microstamped Patterns on Surfaces and Derivative Articles," by Kumar, et al., now U.S. Pat. No. 5,512,131, issued Apr. 30, 1996; priority to International Patent Application No. PCT/US96/03073, filed Mar. 1, 1996, entitled "Microcontact Printing on Surfaces and Derivative Articles," by Whitesides, et al., published as WO 96/29629 on Jun. 26, 1996; U.S. patent application Ser. No. 09/004, 583, filed Jan. 8, 1998, entitled "Method of Forming Articles Including Waveguides via Capillary Micromolding and Microtransfer Molding," by Kim, et al., now U.S. Pat. No. 6,355,198, issued Mar. 12, 2002; International Patent Application No. PCT/US01/16973, filed May 25, 2001, entitled "Microfluidic Systems including Three-Dimensionally Arrayed Channel Networks," by Anderson, et al., published as WO 01/89787 on Nov. 29, 2001; U.S. Provisional Patent Application Ser. No. 60/392,195, filed Jun. 28, 2002, entitled "Multiphase Microfluidic System and Method," by Stone, et al.; U.S. Provisional Patent Application Ser. No. 60/424,042, filed Nov. 5, 2002, entitled "Method and Apparatus for Fluid Dispersion," by Link, et al.; U.S. Provisional Patent Application Ser. No. 60/461,954, filed Apr. 10, 2003, entitled "Formation and Control of Fluidic Species," by Link, et al.; International Patent Application No. PCT/US03/ 20542, filed Jun. 30, 2003, entitled "Method and Apparatus for Fluid Dispersion," by Stone, et al., published as WO 2004/002627 on Jan. 8, 2004; U.S. Provisional Patent Application Ser. No. 60/498,091, filed Aug. 27, 2003, entitled "Electronic Control of Fluidic Species," by Link, et al.; International Patent Application No. PCT/US2004/010903, filed Apr. 9, 2004, entitled "Formation and Control of Fluidic Species," by Link, et al., published as WO 2004/091763 on Oct. 28, 2004; International Patent Application No. PCT/US2004/027912, filed Aug. 27, 2004, entitled "Electronic Control of Fluidic Species," by Link, et al., published as WO 2005/021151 on Mar. 10, 2005; U.S. patent application Ser. No. 11/024,228, filed Dec. 28, 2004, entitled "Method and Apparatus for Fluid Dispersion," by Stone, et al., published as U.S. Patent Application Publication No. 2005-0172476 on Aug. 11, 2005; U.S. Provisional Patent Application Ser. No. 60/659,045, filed Mar. 4, 2005, entitled "Method and Apparatus for Forming Multiple Emulsions," by Weitz, et al.; U.S. Provisional Patent Application Ser. No. 60/659,046, filed Mar. 4, 2005, entitled "Systems and Methods of Forming Particles," by Garstecki, et al.; and U.S. patent application Ser. No. 11/246,911, filed Oct. 7, 2005, entitled "Formation and Control of Fluidic Species," by Link, et al.

The following examples are intended to illustrate certain embodiments of the present invention, but do not exemplify the full scope of the invention.

Example 1

This example illustrates the formation of a semi-permeable shell around aqueous cell-laden drops, e.g., a microcapsule, that allows the transfer of the drops from the (fluorinated) oil phase to culture medium for continued supply of nutrients to the encapsulated cells within the microcapsules. These may be used for long-term incubation of cells on a single-cell level. Furthermore, cell-laden microcapsules dispersed in water would allow the use of commercial flow cytometry equipment such as FACS (fluorescently-activated cell sorting) to analyze and sort the cell/capsule populations.

Providing an impermeable barrier to the aqueous drops is important, for example, to keep distinct drugs contained within their drops in drug screening applications, prevent protein transfer between drops in single-cell biological assays, or to avoid DNA cross-contamination between drops with different cells after lysis and before DNA sequencing, etc. Additionally, while the high oxygen permeability of the fluorinated oils ensures good oxygen supply to encapsulated cells, other nutrition requirements that are necessary for cell survival in the drops may be limited to the initial amount encapsulated within the droplet.

A number of distinct types of oils exist that are immiscible with water, as well as with each other. Such oils include hydrocarbon oils, fluorinated oils, and silicone oils. Fluorinated oils, also called fluorocarbons, such as the commercial Engineered Fluids HFE-7500, HFE-7100, or Fluoroinert FC-40, are chemically and biologically inert and, therefore, widely used in droplet-based biological assays as the continuous phase. In droplet-based assays, aqueous droplets containing, for examples, cells and biological reagents are produced as a dispersion in fluorinated oils. The high oxygen permeability of many fluorinated oils allows for good cell viability inside the drops during prolonged incubation. The separation and compartmentalization of individual or groups of cells in droplets allows for the study of biological functions and cellular activity on a cell-by-cell level, as well as the high throughput screening of biologically active materials such as drugs and their impact on cells.

This example illustrates emulsion stabilizing random copolymers of one or more hydrophobic (meth)acrylate or (meth)acrylamide copolymerized with one or more hydrophilic (meth)acrylate or (meth)acrylamide in a random copolymer architecture. One such copolymer is shown in FIG. 1A. Some non-limiting examples of such copolymers include poly(1H,1H,2H,2H-perfluorodecyl(meth)acrylate-co-3-(acrylamido)phenylboronic acid), herein further abbreviated as PFDMA-APBA; poly(2,2,3,3,4,4,4-heptafluorobutyl methacrylate-co-3-(acrylamido)phenylboronic acid), herein further abbreviated as PFBMA-APBA; poly(ethylmethacrylate-co-3-(acrylamido)phenylboronic acid), herein further abbreviated as PEMA-APBA; PFDA-APBA, obtained from the monomers 1H,1H,2H,2H-heptadecafluorodecyl acrylate and 3-(acrylamido)phenyl boronic acid; and poly(hexylacrylate-co-3-(acrylamido)phenylboronic acid), herein abbreviated as PHA-APBA, and poly(styrene-co-4-vinylphenylboronic acid), herein abbreviated as PS-VPBA. The (meth) and (M) addition describes the possibility of using either acrylic or methacrylic monomers of the same pendant side groups.

Figure 2A:
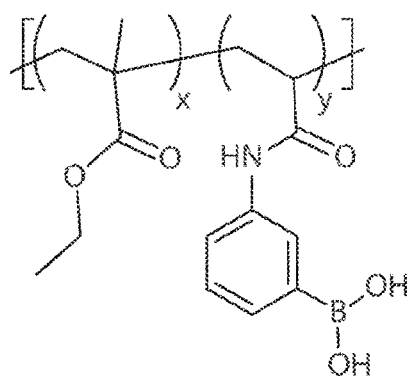
FIGS. 2A-2D illustrate certain copolymers and their properties, in another set of embodiments.
Figure 2B:
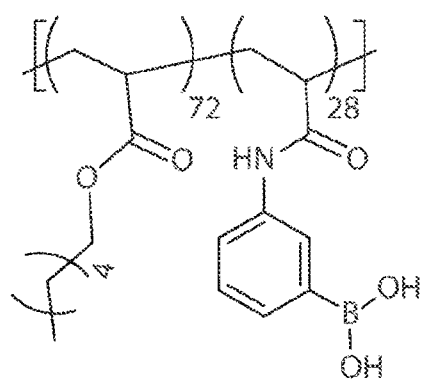
Figure 3A:
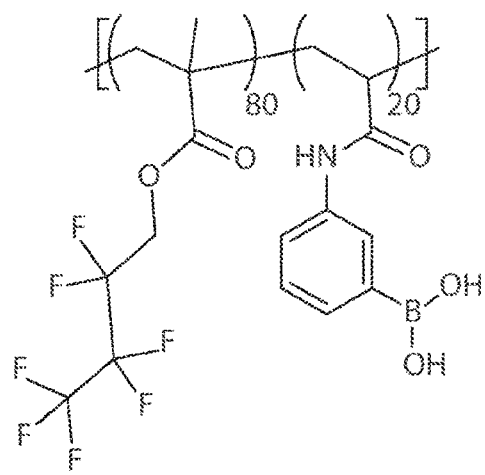
FIGS. 3A-3D illustrate certain copolymers and their properties, in yet another set of embodiments.

Chemical structures of some of these copolymers are shown in FIGS. 2A-2B and 3A. The copolymers are obtained from free-radical polymerization, which incorporates the monomers in a random order during chain growth. Hence, the polymers are random copolymers of fluorophilic or lipophilic and hydrophilic monomers.

Figure 1B:
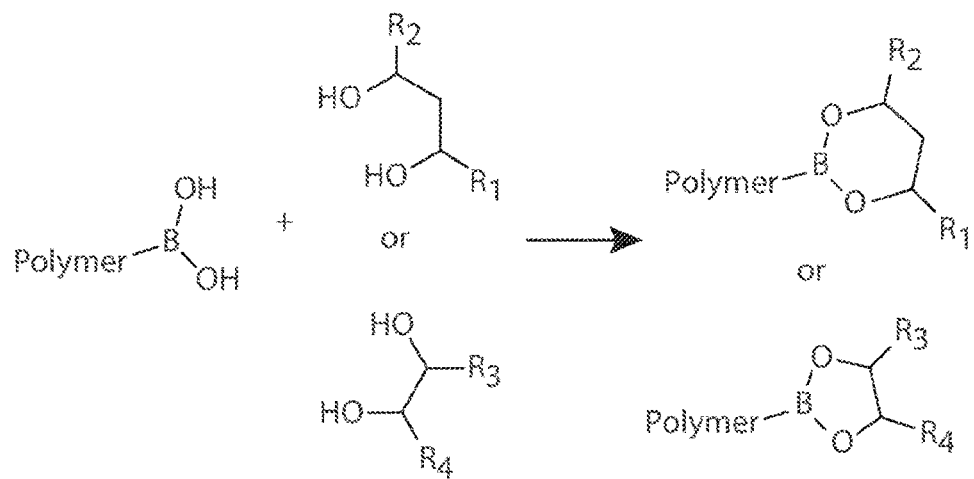
Figure 1C:
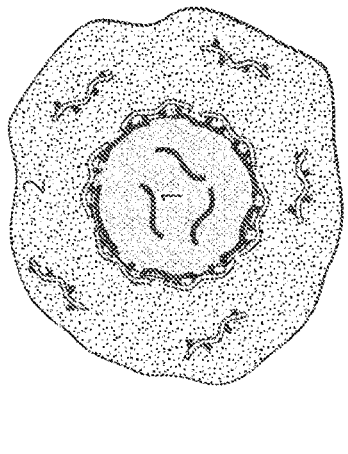
Figure 1E:
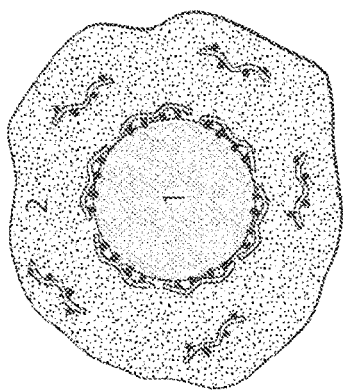
Figure 1D:
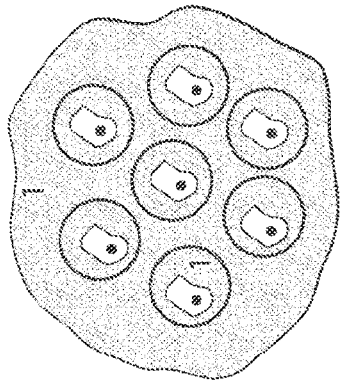
Figure 1F:
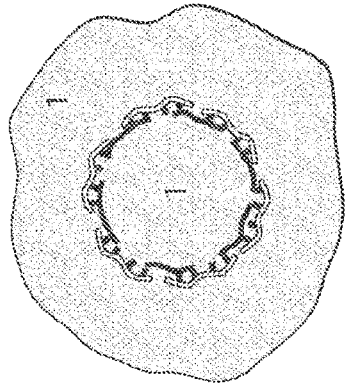

These copolymers can be used as stabilizing surfactants in water-in-fluorocarbon (W/F) and water-in-hydrocarbon emulsion drops, as illustrated in FIG. 1C, including the encapsulation of cells within the aqueous drops with high cell viability. Furthermore, the reversible reaction of boronic acids with 1,2- and 1,3-diols and polyols such as glucose, di-, oligo, and polysaccharides, catechol, as well as polyvinyl alcohol (PVA), allows the formation of boronic ester bonds of the surfactant polymer, as illustrated in FIG. 1B. The presence of polyols such as PVA in the aqueous phase/drop causes the formation of a cross-linked polymer shell at the water-oil interface, as illustrated in FIG. 1D. The interfacial films increase the emulsion stability and decrease the molecular exchange between drops, as well as allows the transfer of the drops as capsules to aqueous media, as illustrated in FIGS. 1E and 1F.

FIG. 1 illustrates the chemical structures of (FIG. 1A) a fluoro-boronic acid (meth) acrylic copolymer and (FIG. 1B) the boronic ester formation with 1,2- and 1,3-diols. FIGS. 1C and 1D illustrate a schematic representation of the surface activity of the PFDMA-APBA copolymer in water-in-fluorocarbon W/F emulsions (FIG. 1C) without and (FIG. 1D) with polyol in the water drops that causes interfacial film formation. The interfacial film formation allows the transfer of the aqueous drops to an aqueous medium (FIG. 1E), which can allow for applications such as the retention of the compartmentalization of cargo such as single cells inside water-dispersed capsules.

Example 2

Figure 2C:
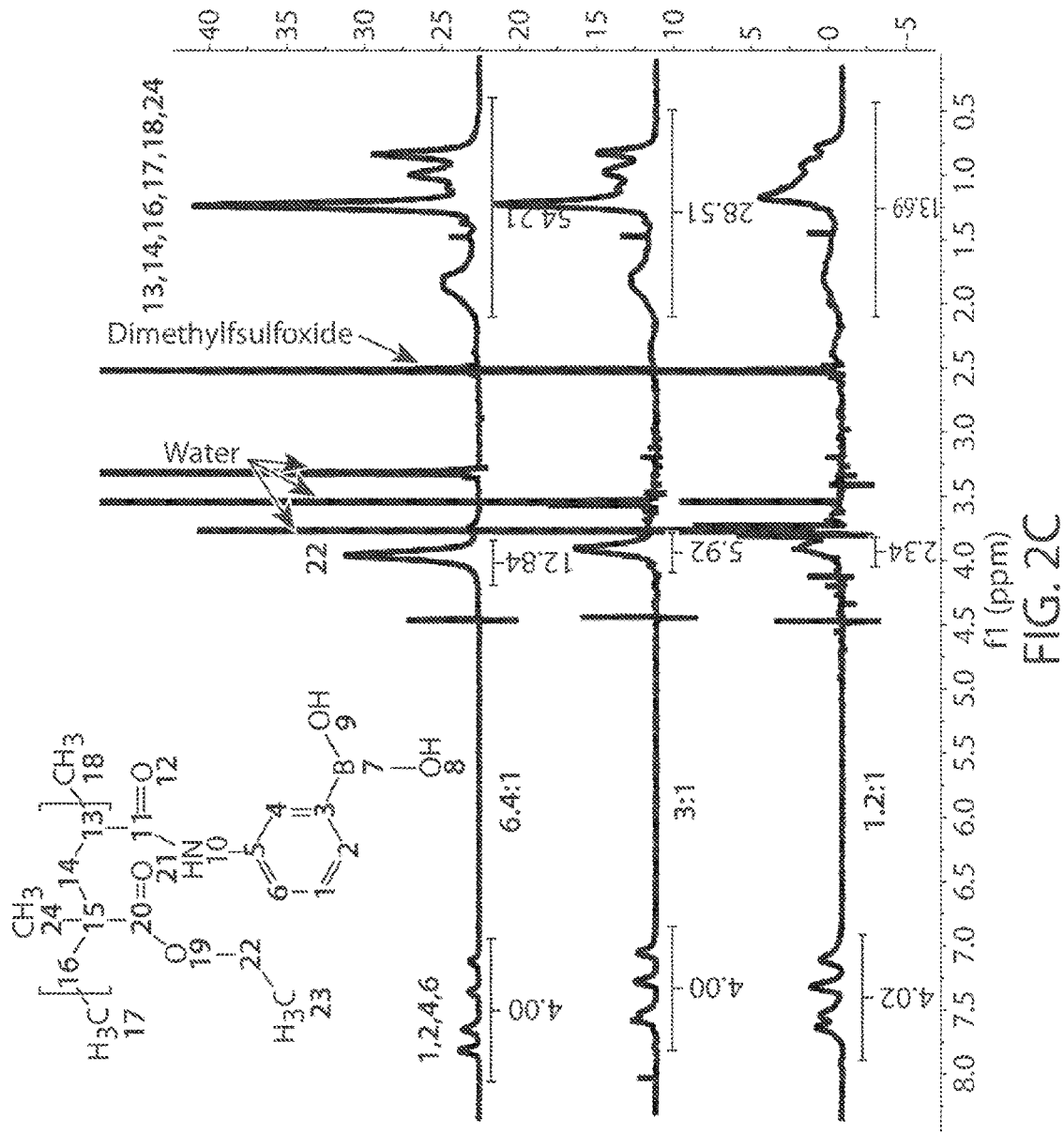
Figure 2D:
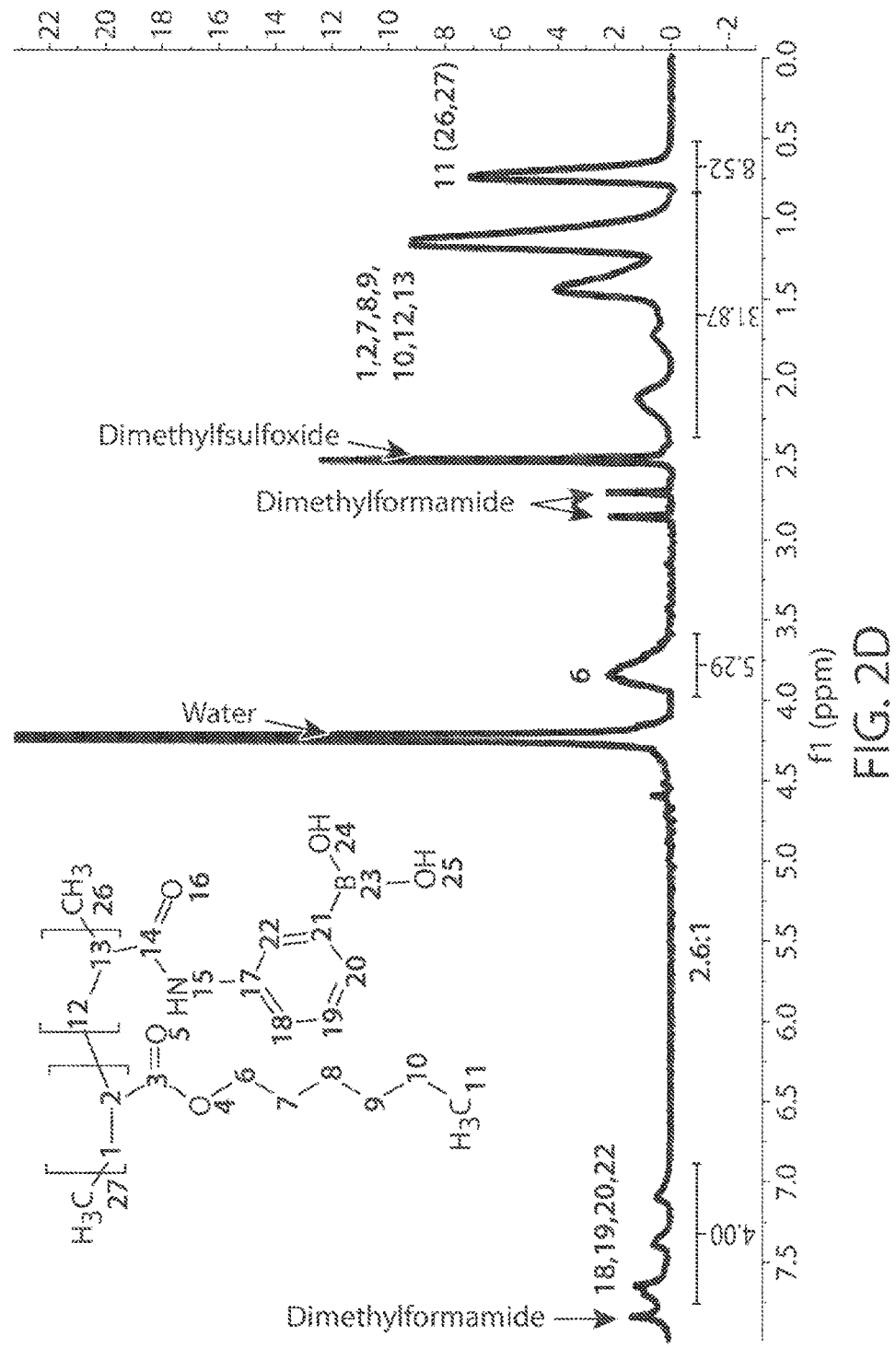

This example illustrates various lipophilic-hydrophilic copolymers. These copolymers containing hydrophilic and hydrophobic comonomers were polymerized using free radical polymerization. The polymerization method typically yielded random copolymers with random incorporation of the two distinct monomers along the polymer chain. The composition of the copolymers depended on the ratio of the monomers added to the polymerization solution. As one example, the lipophilic-hydrophilic copolymers of ethylmethacrylate (EMA) and hexylacrylate (HA) with 3-acrylamidophenylboronic acid (APBA) were obtained with varying monomer molar ratios. The ratio of the monomers was confirmed using $^1$H-NMR as shown in FIGS. 2C and 2D. Copolymers PEMA-APBA with different compositions were dissolved in the hydrophobic hydrocarbons benzyl alcohol, 1-butanol, and ethyl acetate. The copolymer PHA-APBA with an 72:28 monomer ratio was dissolved in the hydrophobic hydrocarbons benzyl alcohol and 1-octanol, and mixtures thereof with olive oil.

Figure 4A:
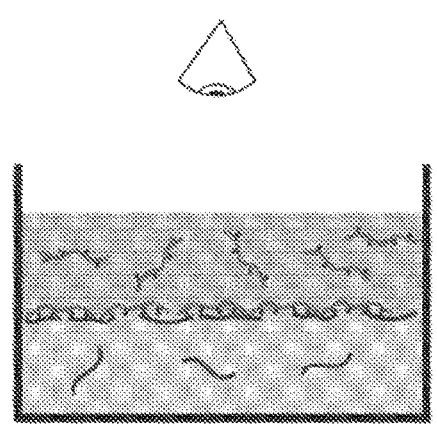
FIGS. 4A-4F illustrate interfacial film formation, in one set of embodiments.
Figure 4B:
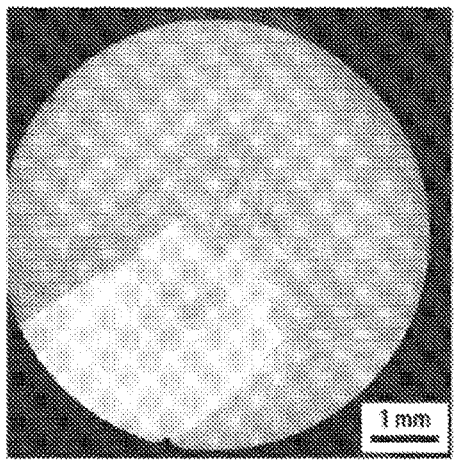
Figure 4C:
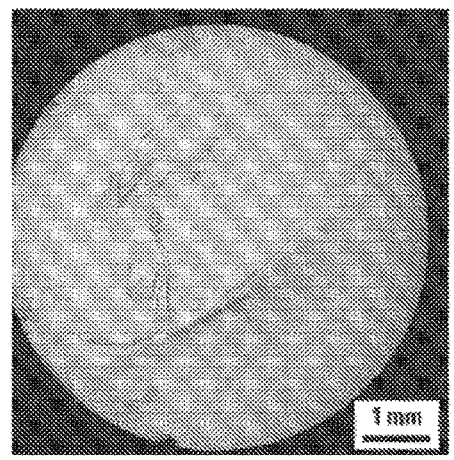
Figure 4D:
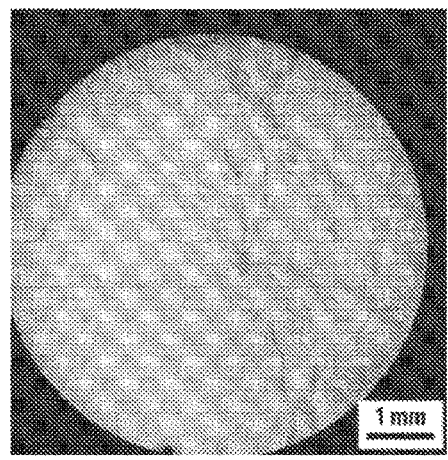
Figures 4E, 4F:
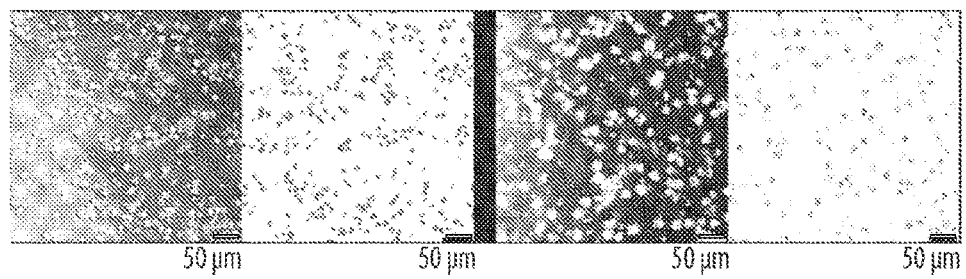

FIG. 2A illustrates the chemical structure of the lipophilic boronic acid copolymers PEMA-APBA (FIG. 2A) and PHA-APBA (FIG. 2B). $^1$H-NMR spectra of (FIG. 2C) the lipophilic boronic acid copolymers PEMA-APBA with different monomer ratios indicated under each trace (taken in deuterated dimethylsulfoxide), and (FIG. 2D) PHA-APBA (taken in deuterated dimethylsulfoxide). The numbers above the traces in (FIGS. 2C and 2D) indicate the peaks corresponding to the protons in the polymer indicated with the associated numbers in the chemical structure (insets). Solvent peaks are indicated in the spectra by full name. To test film formation of the copolymer PEMA-APBA with interfacing aqueous solutions of polyols, benzyl alcohol solutions of the copolymers with different monomer compositions were layered with 2 wt % PVA solutions in DMEM in wells of 96-well plates, as illustrated in FIG. 4A. The film formation for all the polymers at the aqueous-hydrocarbon interface was confirmed with optical microscopy, as shown in FIGS. 4B-4D. The pink color of the DMEM and the wrinkling of the interfacial films allowed the facile observation of the film formation. To test if the lipophilic boronic acid polymers such as PEMA-APBA were suitable for drop-based cell work, cell dispersions in DMEM were interfaced with hydrocarbon solvents for the copolymers such as benzyl alcohol and 1-butanol. A live-dead assay using specific fluorescent dyes indicates that K-562 cells die within 10 minutes after interfacing the organic solvents with the cell dispersion, as shown in FIGS. 4E and 4F (scale bars 50 microns).

FIG. 4A shows a schematic of setup for testing the interfacial film formation between solutions of PEMA-APBA in benzyl alcohol or butanol and PVA in water. FIGS. 4B-4D illustrate optical micrographs of the films formed between PEMA-APBA solutions in benzyl alcohol (5 wt %) and 2 wt % aqueous PVA solutions in DMEM with EMA: APBA monomeric ratios of (FIG. 4B) 1.2:1, (FIG. 4C) 3:1, and (FIG. 4D) 6.4:1. FIGS. 4E and 4F each show (left) a brightfield microscopy image of cells and (right) a fluorescence image of dead staining dye (no cells were alive in this test), of cell dispersions in DMEM interfacing (FIG. 1E) 1-butanol and (FIG. 1F) benzyl alcohol.

The lipophilic-hydrophilic copolymer PHA-APBA dissolved in hydrocarbons such as 1-octanol was expected to populate at the interface of the hydrocarbons and water, due to the hydrophilicity of the boronic acid monomers, as illustrated in FIG. 1C, but did not dissolve in water due to the large lipophilic and hydrophobic PHA amounts in the polymer. This interfacial association of the polymer lowered the interfacial energy of the oil-water interface and induced a kinetic barrier to coalescence of water drops dispersed in oil. Thus, the random copolymer effectively acted as a surfactant.

Boronic acids can form reversible bonds with diols and polyols such as glucose, saccharides, and poly(vinyl alcohol) (PVA) through the formation of a cyclic ester, as illustrated in FIG. 1B. In an W/O emulsion containing a polyol such as PVA in the aqueous drop and PHA-APBA as the copolymer surfactant in the hydrocarbon continuous phase such as 1-octanol, the two polymers reacted at the fluid-fluid interface to form a thin, cross-linked polymer shell around the water drop, as illustrated in FIG. 1D. The presence of a solid polymer shell increased the stability of the emulsions, and potentially decreased molecular diffusion from on drops to another, which often causes cross-contamination issues in droplet-based technologies. Homogeneous aqueous droplets containing 2 wt % PVA were dispersed in 1-octanol with 5 wt % PHA-APBA as surfactant in microfluidic drop-makers. The narrow drop size distribution of emulsions obtained from microfluidic drop-making allowed the facile monitoring of droplet stability over time. The drops demonstrated very good stability over time, as shown in FIGS. 10A-10B. The solid film between the water drops and continuous oil phases imparted altered properties to the interface such as buckling upon decrease of droplet volume during drying, as can be seen for some droplets as indicated by the arrows in FIGS. 10A and 10B. Upon drying of the droplets, scanning electron microscopy was performed on the resulting capsules with very thin polymeric shells, as shown in FIGS. 10D, 10E, and 10F. The wrinkling pattern of the polymeric shell formed by the complex between the random amphiphilic copolymer PHA-APBA and PVA at the oil-water interface indicates that the thickness of the shell is below 100 nm, as shown in FIG. 10F.

FIG. 10 shows optical and scanning electron micrographs (SEM) of capsules obtained from aqueous drops containing 2 wt % PVA emulsified in 1-octanol containing 5 wt % PHA-APBA. FIG. 10A shows optical micrographs of the droplets showing homogeneous spherical drops towards the top of the images, and the wrinkling polymer shells from the complex formed between PVA and PHA-APBA at the interface surrounding the drops are apparent for the partially dried drops towards the bottom of the images, some are indicated by arrows. FIGS. 10C-E show SEM images of the emulsion drops after drying showing the capsules flattened (FIG. 10C) or crumpled (FIG. 10D) upon drying. The wrinkling pattern observed for the shell in FIG. 10E suggested a polymer shell thickness of less than 100 nm for these capsules.

Example 3

Figure 3B:
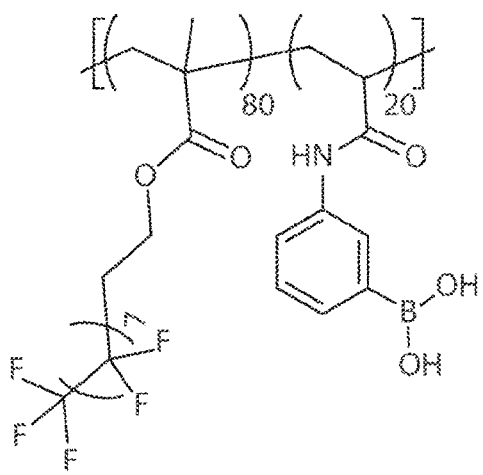
Figure 3C:
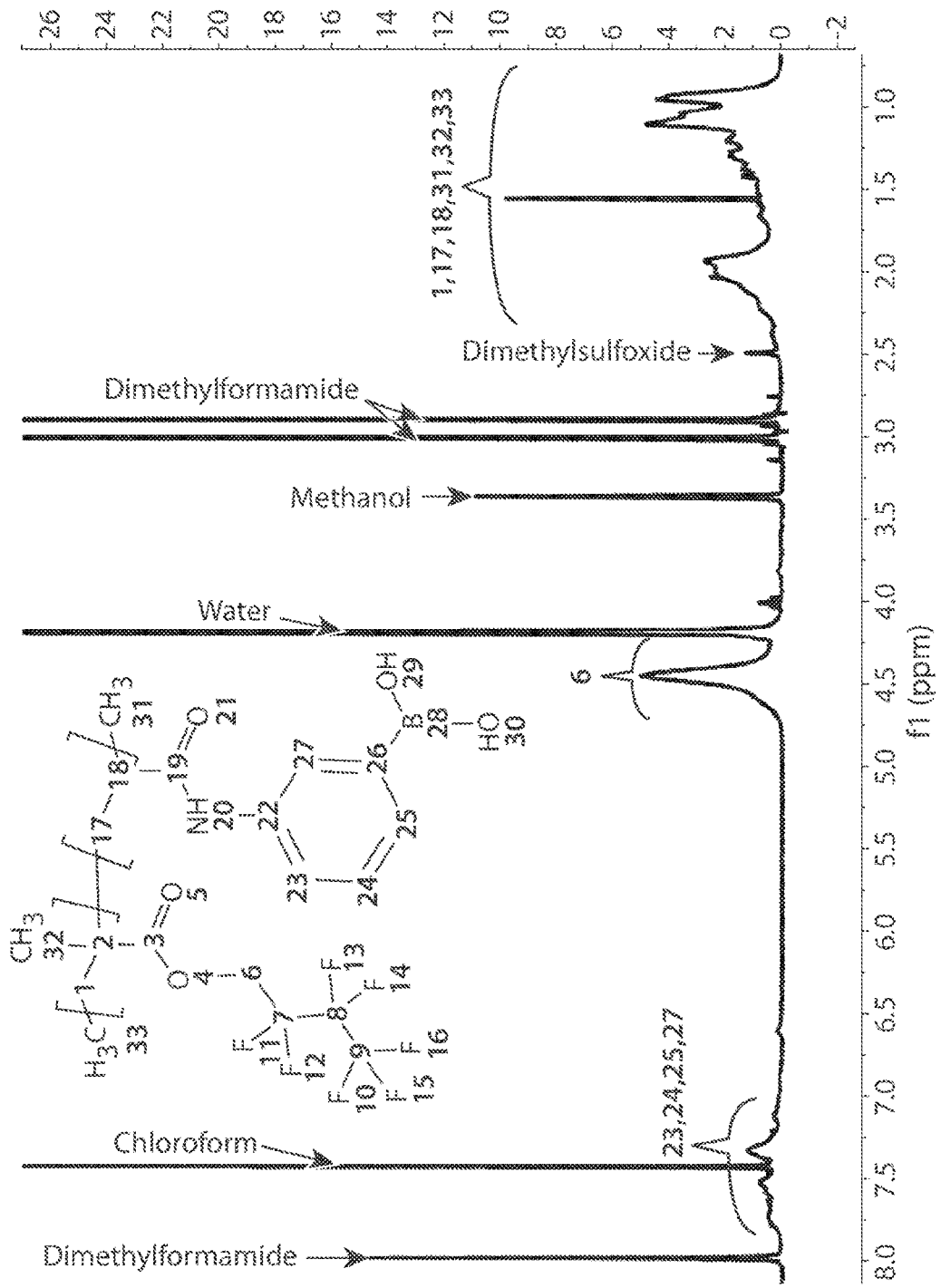
Figure 3D:
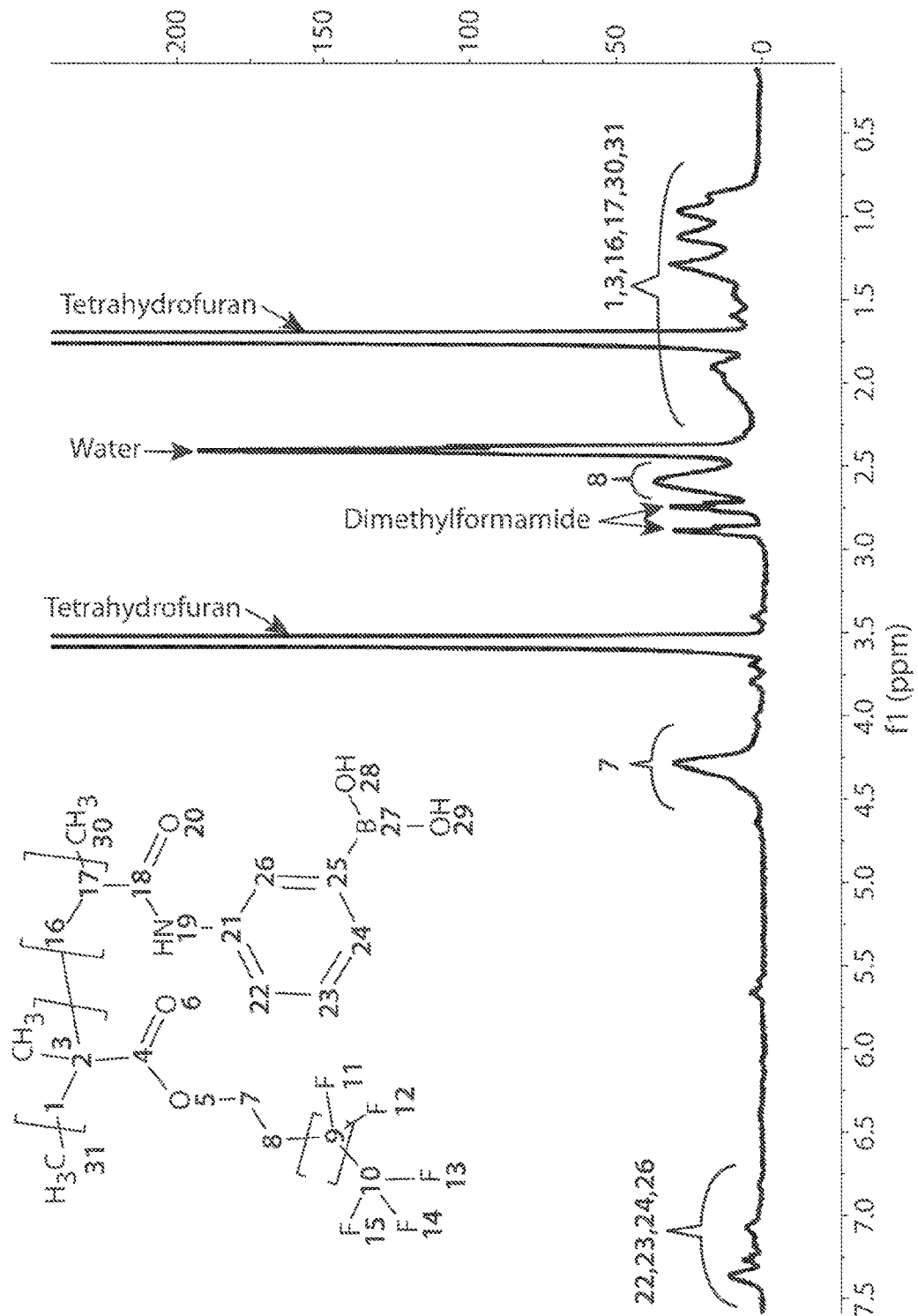

This example illustrates fluorophilic-hydrophilic copolymers. This example shows hydrophilic-hydrophobic copolymer emulsion stabilizer and interfacial film former using the fluorophilic-hydrophilic copolymers of 1H,1H,2H,2H-perfluorodecyl methacrylate (FDMA) and 2,2,3,3,4,4,4-heptafluorobutyl methacrylate with 3-acrylamidophenylboronic acid (APBA), which were obtained with monomer molar ratios of 80:20. The ratios of the monomers were confirmed using $^1$H-NMR as shown in FIGS. 3B and 3C. The copolymer PFDMA-APBA dispersed in the fluorinated oils HFE-7500, HFE-7100, and Fluorinert™ FC-40 as translucent solutions, indicating some micelle of nano-aggregate formation. No precipitation, formation of heterogeneities or settlement was observed over weeks of storage at concentrations of 3 wt %. It is believed that the hydrophilic boronic acid groups of the polymer chains associated with each other in fluorinated liquids, forming nano-assemblies such as micelles in the fluorocarbons. This phenomenon was expected to be dependent on the copolymer composition (monomer ratio) and the exact fluorophilic and hydrophilic comonomers used, as well as co-solvents in the fluorocarbon oil.

FIG. 3 illustrates the chemical structures of the fluoro-boronic acid copolymers PFBMA-APBA (FIG. 3A) and PFDMA-APBA (FIG. 3B). FIGS. 3C-3D illustrate $^1$H-NMR spectra of the fluoro-boronic acid copolymers PFBMA-APBA (FIG. 3C), taken in deuterated chloroform and methanol), and PFDMA-APBA (FIG. 3D), taken in deuterated tetrahydrofuran. The numbers indicate the peaks corresponding to the protons in the polymer indicated with the associated numbers in the chemical structure (insets). Solvent peaks are indicated in the spectra by full name. The ratio of the integrated area under the aromatic peaks of the boronic acid monomer and the ester-adjacent protons (FIG. 3C: #6, FIG. 3D: #7) is 1:2, corresponding to a composition of 80:20 between the fluorinated and the boronic monomers.

Example 4

The fluorophilic-hydrophilic copolymers were expected to populate at the interface of fluorocarbons and water, due to the hydrophilicity of the boronic acid monomers, as illustrated in FIG. 1C, but didn't dissolve in water due to the large fluorophilic and hydrophobic FDMA amounts in the polymer. This interfacial association of the polymer lowered the interfacial energy of the oil-water interface and induced a kinetic barrier to coalescence of water drops dispersed in oil. Thus, the random copolymer effectively acted as a surfactant.

Figure 5A:
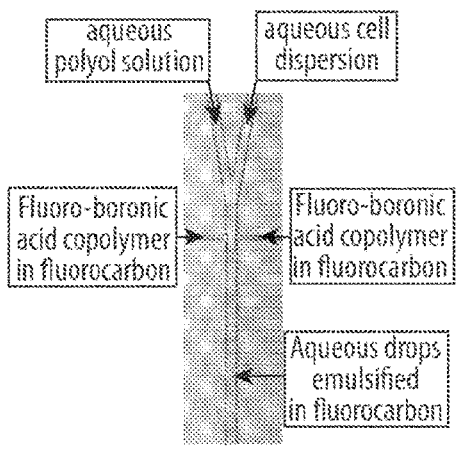
FIGS. 5A-5F illustrate droplet stability, in accordance with another set of embodiments.
Figure 5B:
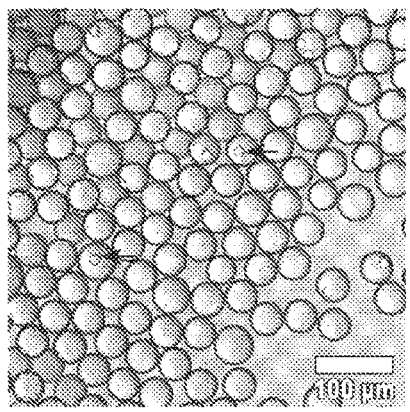

Homogeneous cell-containing aqueous droplets were dispersed in HFE-7500 with 3 wt % PFDMA-APBA as surfactant in microfluidic drop-makers, as shown in FIG. 5A. The narrow drop size distribution of emulsions obtained from microfluidic drop-making allowed the facile monitoring of droplet stability over time. An aqueous droplet contained fetal bovine serum (FBS), bovine serum albumin (BSA), or Iodixanol (OptiPrep™). The drops kept their narrow size distribution even after incubation at 37° C. for 1 day, as shown in FIG. 5B, demonstrating the highly stabilizing surface-active property of this copolymer for water-in-fluorocarbon (W/F) emulsions. After transferring the aqueous emulsion drops and their cells to an aqueous phase (so-called "breaking" of the emulsion) with perfluorooctanol, the encapsulated cells showed a high viability and survival rate, demonstrating the biocompatibility of this copolymer as surfactant in W/F emulsions.

Figure 5C:
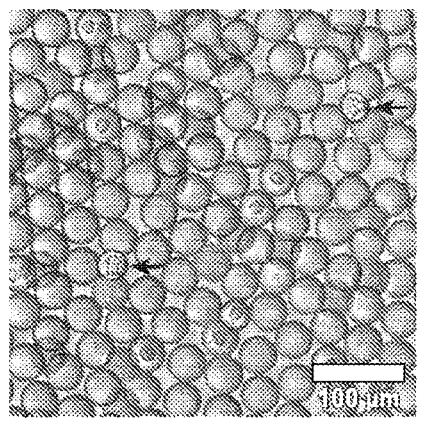
Figure 5D:
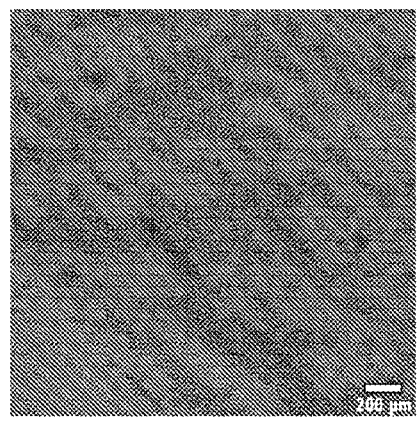

Boronic acids can form reversible bonds with diols and polyols such as glucose, saccharides, and polyvinyl alcohol (PVA) through the formation of a cyclic ester, as illustrated in FIG. 1B. In an W/F emulsion containing a polyol such as PVA in the aqueous drop and PFDMA-APBA as the copolymer surfactant in the fluorocarbon continuous phase, the two polymers reacted at the fluid-fluid interface to form a thin, cross-linked polymer shell around the water drop, as illustrated in FIG. 1D. The presence of a solid polymer shell increased the stability of the emulsions, and potentially decreased molecular diffusion from on drops to another, which often causes cross-contamination issues in droplet-based technologies. Homogeneous drops containing 2 wt % PVA that were fabricated the same way as above also demonstrated very good stability on incubation, as shown in FIGS. 5C and 5D. The solid film between the water drops and continuous oil phases imparted altered properties to the interface such as buckling upon decrease of droplet volume during incubation, as can be seen for some droplets as indicated by the arrows in FIG. 5C.

Figure 5E:
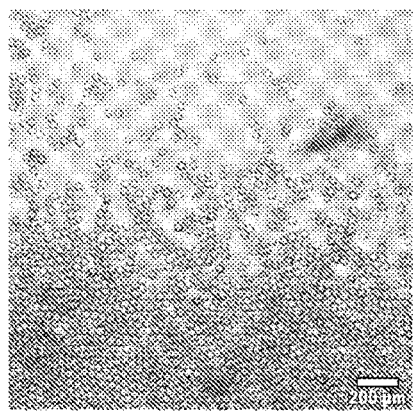
Figure 5F:
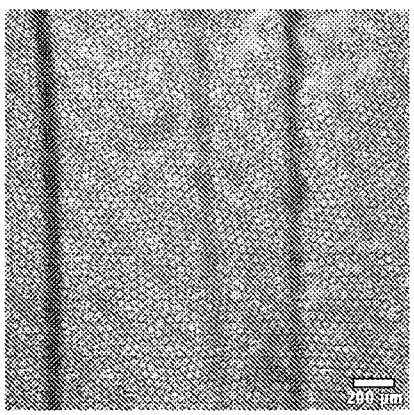

Furthermore, the interfacial film decreased the exchange rate of surfactant dissolved in the continuous phase and surfactant molecules at the water-oil interface. To demonstrate this permanent stabilization of the W/F emulsions, the continuous fluorocarbon phase was washed with pure HFE-7500 three times to remove any excess dissolved fluoro-boronic acid copolymer surfactant. The uniform size distribution of the drops after excess copolymer surfactant removal and no visible coalescence of drops demonstrated the long-term stabilization effect of the interfacial polymer film formed between the PVA and the fluoro-boronic acid copolymer, as shown in FIG. 5E. Even at decreased concentrations of the polymers, 1 wt % PVA in the aqueous drops and 1.2 wt % PFDMA-APBA in the continuous HFE-7500 phase, the emulsions demonstrated remarkable stability after removal of excess copolymer surfactant in the oil phase, as shown in FIG. 5F.

FIG. 5 shows optical micrographs of (FIG. 5A) microfluidic water-in-fluorocarbon (W/F) droplet formation and FIGS. 5B-5F) W/F drops under different conditions: (FIG. 5B) cells encapsulated in aqueous drops emulsified in HFE-7500 containing 3 wt % PFDMA-APBA after 1 day of incubation at 37° C., arrows indicate cells in drops; (FIG. 5C) cells encapsulated in aqueous drops containing 2 wt % PVA emulsified in HFE-7500 containing 3 wt % PFDMA-APBA after 1 day of incubation at 37° C., arrows indicate buckling of deflated drops/capsules; (FIG. 5D) Aqueous drops containing 2 wt % PVA emulsified in HFE-7500 containing 3 wt % PFDMA-APBA after 1 day of incubation at room temperature; (FIG. 5E) Aqueous drops containing 2 wt % PVA emulsified in HFE-7500 containing 3 wt % PFDMA-APBA after 1 day of incubation at room temperature and removal of excess PFDMA-APBA from the HFE-7500; and (FIG. 5F) Aqueous drops containing 1 wt % PVA emulsified in HFE-7500 containing 1.2 wt % PFDMA-APBA after 1 day of incubation at room temperature and removal of excess PFDMA-APBA from the HFE-7500.

Example 5

Figure 6A:
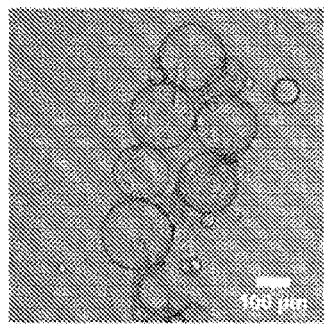
FIGS. 6A-6I illustrate encapsulation of droplets, in yet another set of embodiments.
Figure 6B:
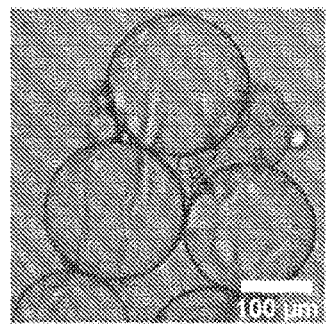
Figure 6C:
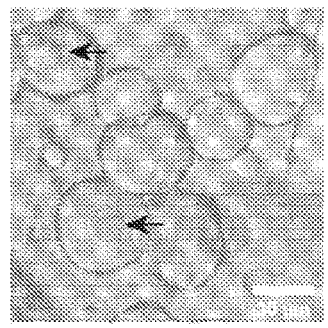
Figure 6D:
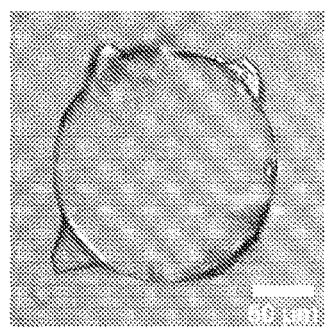
Figure 6E:
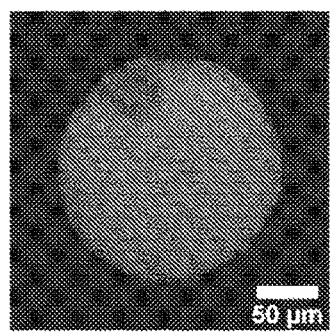
Figure 6F:
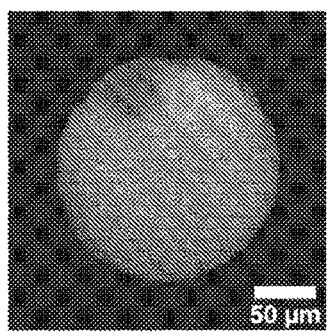

The formation of a polymer film around the water drop allows for the transfer of the water drops to other continuous phases, such as aqueous media, without losing the individual compartmentalization of the content of the drops, as illustrated in FIGS. 1E and 1F. If transferred to an aqueous continuous phase, the resulting architecture represented a capsule with an aqueous drop surrounded by a cross-linked polymer shell dispersed in aqueous medium. The cross-linked polymer shell comprised the linear boronic acid-containing copolymer that is cross-linked with a polyol such as PVA. Upon transfer of the drops described above containing 2 wt % PVA in the aqueous drop and 3 wt % PFDMA-APBA in the continuous HFE-7500 phase, microcapsules with a solid shell were obtained as shown in FIG. 6. Excess polymer formed around the capsules during transfer if it is not cleaned out from the HFE-7500 before transfer, as can be seen in FIGS. 6A and 6C. Cells that were encapsulated in the initial water drop stayed encapsulated in the microcapsules during transfer of the capsules to PBS buffer, as shown in FIG. 6C.

Figure 6G:
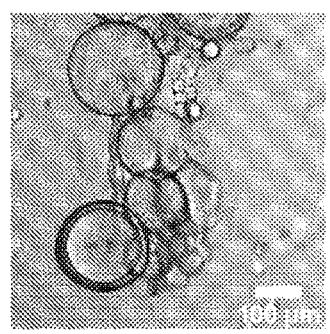
Figure 6H:
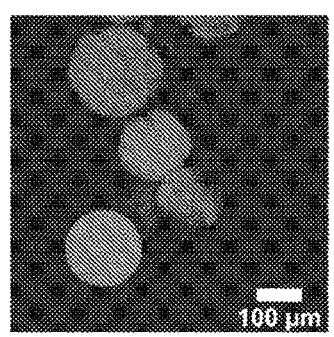
Figure 6I:
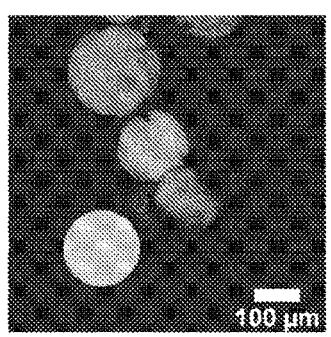
Figure 7A:
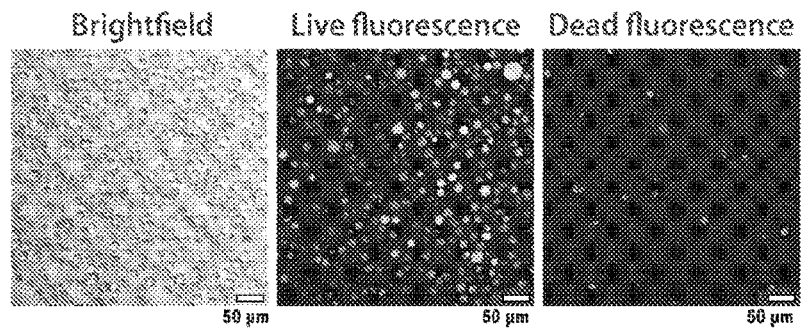
FIGS. 7A-7D illustrate the viability of cells contained within certain embodiments of the invention.
Figure 7B:
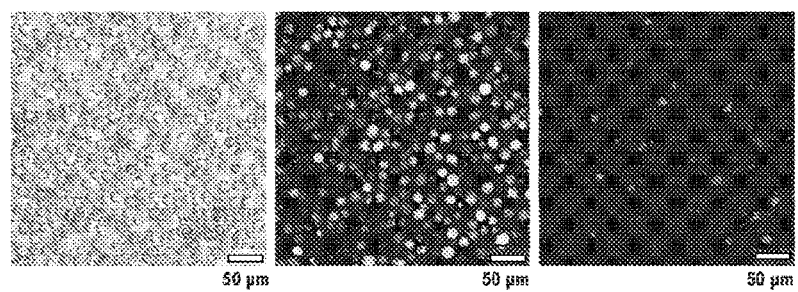
Figure 7C:
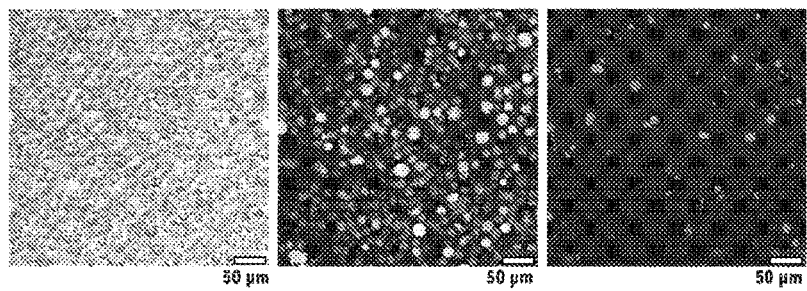
Figure 7D:
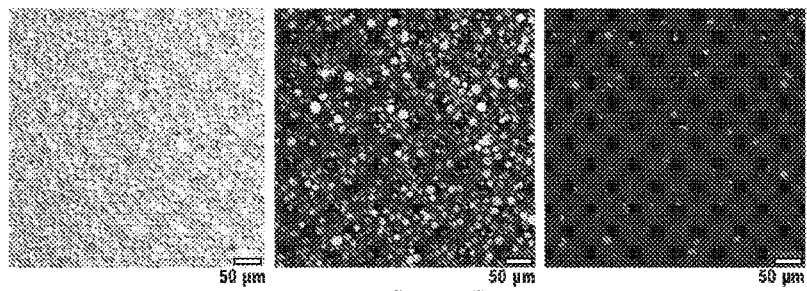

The encapsulation of cells into water-dispersed microcapsules will allow the use of common flow cytometry equipment such as FACS (Fluorescence-activated cell sorting). Furthermore, exchange of nutrients between the continuous aqueous phase and the interior of the microcapsule increased the time a cell could be incubated in its microcompartments as compared to W/F droplets, in which nutrients are not replenished and the cells starve as soon as all nutrients are depleted inside the drops. Molecular dyes that were encapsulated inside the aqueous drops exhibited some diffusion through the shell into the aqueous phase after transfer from the oil phase. The shells demonstrated a higher permeability to the small dye sulforhodamine B (559 g/mol) than the larger fluorescein-labeled dextran (250 kg/mol), as shown in the confocal laser-scanning fluorescence micrographs in FIGS. 6D-6I. The difference in fluorescence between capsules with and without additional HFE-7500 oil shells demonstrated the increased permeability of the capsules to the molecular solutes for capsules without additional oil shell, as shown in FIG. 6G-6I. The permeability of the polymer shell was expected to depend not only on size of the solute, but significantly on the copolymer composition, such as the percentage of boronic acid monomer, the copolymer and polyol (PVA) concentration, the nature of the polyol and its affinity to react with boronic acids, as well as the pH. At low pH, the reaction between boronic acids and polyols was reversed, removing the cross-links in the polymer shells. Alternatively, the addition of a competing diol such as ethylene glycol, glucose, or catechol could release the cross-links due to the high chemical reversibility of the boronic ester formation reaction.

FIG. 6A illustrates optical micrographs of polymer-encapsulated water droplets containing 2 wt % PVA in PBS buffer that where produced by emulsification in HFE-7500 containing 3 wt % PFDMA-APBA and subsequent transfer to PBS. FIG. 6C shows capsules that contain cells in the aqueous core as indicated by the arrows. FIGS. 6D-6I show confocal laser-scanning transmission bright field (FIGS. 6D and 6G) and fluorescence (FIGS. 6E, 6F, 6H, and 6I) micrographs of the same microcapsules as in (FIGS. 6A and 6B). The aqueous phase contained sulforhodamine B (fluorescence measured at 600-640 nm in FIGS. 6E and 6H) and FITC-dextran (250 kg/mol, fluorescence measured at 490-530 nm in FIGS. 6F and 6I). The bottom capsule in FIGS. 6G-6D retained an oil shell (HFE-7500) around its polymer shell during transfer and its increased fluorescence intensity as compared to the capsules in the same image indicates some permeability of the capsules shell to the fluorescent probes.

Example 6

The biocompatibility of the emulsion-stabilizing and interfacial film forming fluorophilic boronic acid copolymer PFDMA-APBA was confirmed in this example using live-dead assays with specific fluorescent dyes. Three concentrations of PVA in the cell dispersion were tested: 0 wt %, 0.2 wt % and 2 wt %. Without PVA in the solution, the cell viability was 89%, with 0.2% PVA we detected 93% of live cells, and with 2% PVA the cell viability was 90%, as shown in FIGS. 7A-7D (scale bars 50 microns).

FIG. 7A-FIG. 7D each show (left) a brightfield microscopy image of cells, (middle) a fluorescence microscopy image of live staining dye and (right) a fluorescence microscopy image of dead staining dye, of cell dispersions in DMEM with (FIG. 7A) 2 wt % PVA, (FIG. 7B) 0.2 wt % PVA, (FIG. 7C) 20 vol % DI-water, and (FIG. 7D) no additive as control.

Example 7

This example illustrates various materials and methods used in the above experiments.

Polymer synthesis and characterization: The lipophilic and fluorophilic (meth)acrylate monomers such as ethylmethacrylate (EMA), hexylacrylate (HA), 1H,1H,2H,2H-perfluorodecyl (meth)acrylate (FD(M)A), or heptafluoro-n-butyl methacrylate (FBMA) were dissolved in a common solvent such as dimethyl formamide (DMF) together with a hydrophilic comonomer such as 3-(acrylamido)phenylboronic acid (APBA) and a radical initiator such as azobisisobutyronitrile (AIBN). The concentration of the monomers in solution was varied between 1 and 50 wt %. The solutions were degassed by bubbling inert gas such as nitrogen through the solution for at least 10 minutes and subsequently sealing the containers. The solutions were heated to 70° C. for at least 12 hours initiate the polymerization and grow the polymers in a free radical polymerization. Some polymers may precipitate from the solvent during the polymerization depending on the monomers, concentration, and composition used. Plymerization was stopped by opening the reaction container and precipitating the polymers in 10 times excess water by volume. The polymers were washed repeatedly with water and methanol and subsequently dried in a vacuum oven to remove unreacted monomer and solvent. The polymer composition was characterized using $^1$H-NMR spectroscopy using a mixture of deuterated solvents such as d-tetrahydrofuran, d-chloroform, d-methanol, and d-dimethyl sulfoxide. The composition of the co-monomers in the polymers was obtained by comparing the aromatic proton peaks of 3-(acrylamido) phenylboronic acid (APBA: 4 peaks around 7-7.8 ppm, 4 protons per monomer) and the oxygen-adjacent methylene group of the lipophilic or fluorophilic (meth)acrylates (broad peak around 3.5-4.5 ppm, 2 protons per monomer), as shown in FIGS. 2C, 2D, 3C, and 3D. Copolymers of PEMA-APBA with compositions of 6.4:1, 3:1, and 1.2:1 EMA:APBA (molar monomer ratios) and PHA-APBA with an HA:APBA molar ratio of 2.6:1 were prepared. The copolymer PEMA-APBA dissolved in common lipophilic solvents up to at least 5 wt % including benzyl alcohol, 1-butanol, and ethyl acetate. The copolymer PHA-APBA dissolved in lipophilic solvents including benzyl alcohol, and mixtures thereof with alkyl oils such as olive oil. The composition of the PFDMA-APBA and PFBMA-APBA copolymers studied was 80 mol % fluorinated methacrylate and 20 mol % ABPA, as shown in FIG. 3. The copolymer PFDMA80-APBA20 formed translucent dispersions in HFE-7500, HFE-7100, and Fluorinert™ FC-40, indicating the formation of nanometer-sized aggregates or micelles in these fluorocarbon oils at 3 wt %.

Another lipophilic boronic acid copolymer is based on poly(styrene). Poly(styrene-co-4-vinylphenylboronic acid) (PS-VPBA) copolymers were prepared in a similar way as described above using dioxane as the solvent. Copolymers of varying monomer compositions, with styrene-to-4-vinylphenylboronic acid ratios of 0.3:1 to 6.7:1, were prepared, as demonstrated by the $^1$H-NMR spectra. $^1$H-NMR was measured in deuterated dimethylsulfoxide at a 1-2 wt % concentration and the monomer ratio is calculated based on the comparison of the peak at 7.3-7.8 ppm that corresponds to two aromatic protons in the 4-vinylphenylboronic acid, and the peaks at 6.5-7.3 ppm that correspond to the other two aromatic protons of the boronic acid monomer and five aromatic protons of the styrene monomers. If the area of the peak at 7.3-7.8 is set to two (corresponding to one 4-vinylphenylboronic acid monomer), the resulting area for the peaks at 6.7-7.3 is first subtracted by two and then divided by five to obtain the amount of styrene monomers per one 4-vinylphenylboronic acid monomer.

Figure 9C:
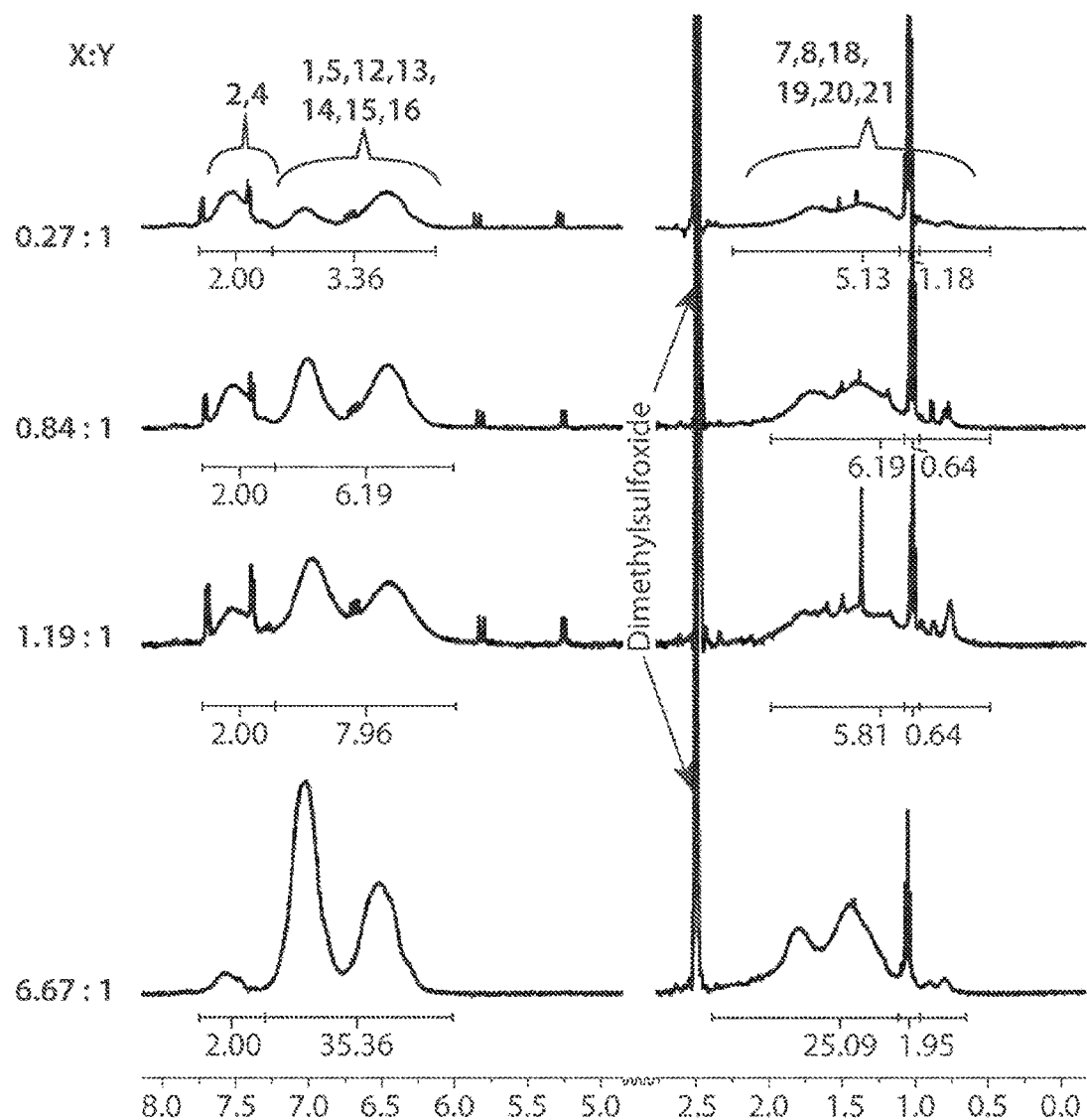

FIGS. 9A and 9B illustrate the chemical structure of the lipophilic boronic acid copolymer PS-VPBA. $^1$H-NMR spectra of (FIG. 9C) the lipophilic boronic acid copolymers PS-VPBA with different monomer ratios indicated next to each trace (taken in deuterated dimethylsulfoxide). The numbers above the traces in (FIG. 9C) indicate the peaks corresponding to the protons in the polymer indicated with the associated numbers in the chemical structure (FIG. 9B). Solvent peaks are indicated in the spectra by full name.

FIGS. 9A and 9B show the chemical structures of poly (styrene-co-4-vinylphenylboronic acid) copolymers with (FIG. 9B) numbered carbons corresponding to numbered peaks in FIG. 9C. FIG. 9C shows proton-NMR spectra of a variety of poly(styrene-co-4-vinylphenylboronic acid) copolymers synthesized with different monomer ratios as indicated on the left of each trace (X=styrene, Y=4-vinylphenylboronic acid). Numbers over peaks correspond to protons bond to numbered carbons in FIG. 9B.

Emulsion fabrication and film formation studies: Emulsions were prepared with dispersed aqueous phases of DI water, phosphate buffered saline (PBS), Dulbecco's Modified Eagle Medium (DMEM) with and without K-562 cells, as well as DMEM with and without PVA (0.1-2 wt %), in some cases containing K-562 cells. In some cases, the aqueous phase contained fluorescent dyes and dye-conjugated macromolecules such as dextran as molecular probes. These aqueous phases were emulsified in fluorocarbon oil such as HFE-7500 containing the copolymer PFDMA-ABPA at up to 3 wt %, or 1-octanol containing PHA-APBA up to 5 wt %. Controlled and homogeneous water-in-fluorocarbon (W/F) and water-in-hydrocarbon (W/O) emulsion drops were fabricated in microfluidic drop-makers that contained a drop-making junction where one or more channels carrying aqueous phases intersect with one or more channels carrying fluorocarbon or hydrocarbon liquids such as HFE-7500 or 1-octanol, respectively. The width and height of the microfluidic channels was on the order of tens of micrometers. The microfluidic drop-makers were fabricated out of poly(dimethylsiloxane) (PDMS) using soft lithography and sealed on one side with a glass slide. Flow rates of the different fluidic phases were in the hundreds of microliters per hour with tunable drops sizes in the tens to hundreds of micrometers. The walls of the microfluidic channels were rendered hydrophobic by immersing them in Aquapel for 1-10 minutes. Alternatively, emulsions were fabricated by shaking a container containing an aqueous phase and a hydrophobic oil. Emulsions were kept at room temperature or were incubated at 37° C. for at least one day to test emulsion stability. Emulsion drops without PVA were coalesced with excess PBS buffer to recover cells from the drops through the addition of the demulsifier perfluorooctanol (PFO) to the fluorocarbon oil. Capsules that formed around aqueous drops containing PVA were transferred to aqueous medium in a similar way. Film formation at the water-oil interface was also studied by layering the two fluid phases on top of each other in a small container and monitoring the film formation with optical microscopy.

Drop and capsule characterization: Emulsion drops and capsules were characterized on optical microscopes, in part using confocal laser-scanning fluorescence microscopes such as the Leica SP5 in bright-field transmission mode and confocal fluorescence mode if fluorescent dyes have been added. Excitation wavelengths of 488 nm and 543 nm were used, and fluorescence intensity was collected at 490-530 nm for fluorescein-based fluorescent probes and 600-640 nm for rhodamine-based probes to avoid emission overlap.

Cell viability: The toxicity of PVA on K-562 cells was tested using CellTracker™ Green CMFDA Dye as a live dye and Sytox red as a dead dye. Three concentrations of PVA were tested: 0%, 0.2% and 2% in DMEM with 10 vol % Fetal Bovine Serum and 1% penicillin streptomycin. Cells were incubated in these solutions at room temperature for 10 min. Without PVA in the solution, the cell viability was 89%, and with 0.2% PVA 93% live cells were detected, and with 2% PVA 90% live cells were detected. K-562 cells were encapsulated in 50 micrometer droplets containing 64 vol % DMEM, 16 vol % FBS, 0.8% penicillin streptomycin with 19.2 vol % optiprep with and without 2 wt % PVA that were dispersed in an oil phase consisting of HFE-7500 with 3 wt % PFDMA-APBA. After encapsulation half of the emulsions were broken by adding 20% PFO into the oil phase, and the water phase is transferred into 500 microliters of PBS. Viability of cells encapsulated in drop containing 0% PVA was measured using CellTracker™ Green CMFDA Dye as a live dye and Sytox red as a dead dye. Cell viability was 89%. The other half of the emulsions was incubated at 37° C. for 1 day, the emulsions were broken by adding 20% PFO into the oil phase, and the water phase is transferred into 500 microliters of PBS. Viability of cells encapsulated in drop containing 0% PVA was measured using CellTracker™ Green CMFDA Dye as a live dye and Sytox red as a dead dye. Cell viability was 54%.

Example 8

Synthesis and Activation of Protected Boronic Acid Copolymer

Figure 11A:
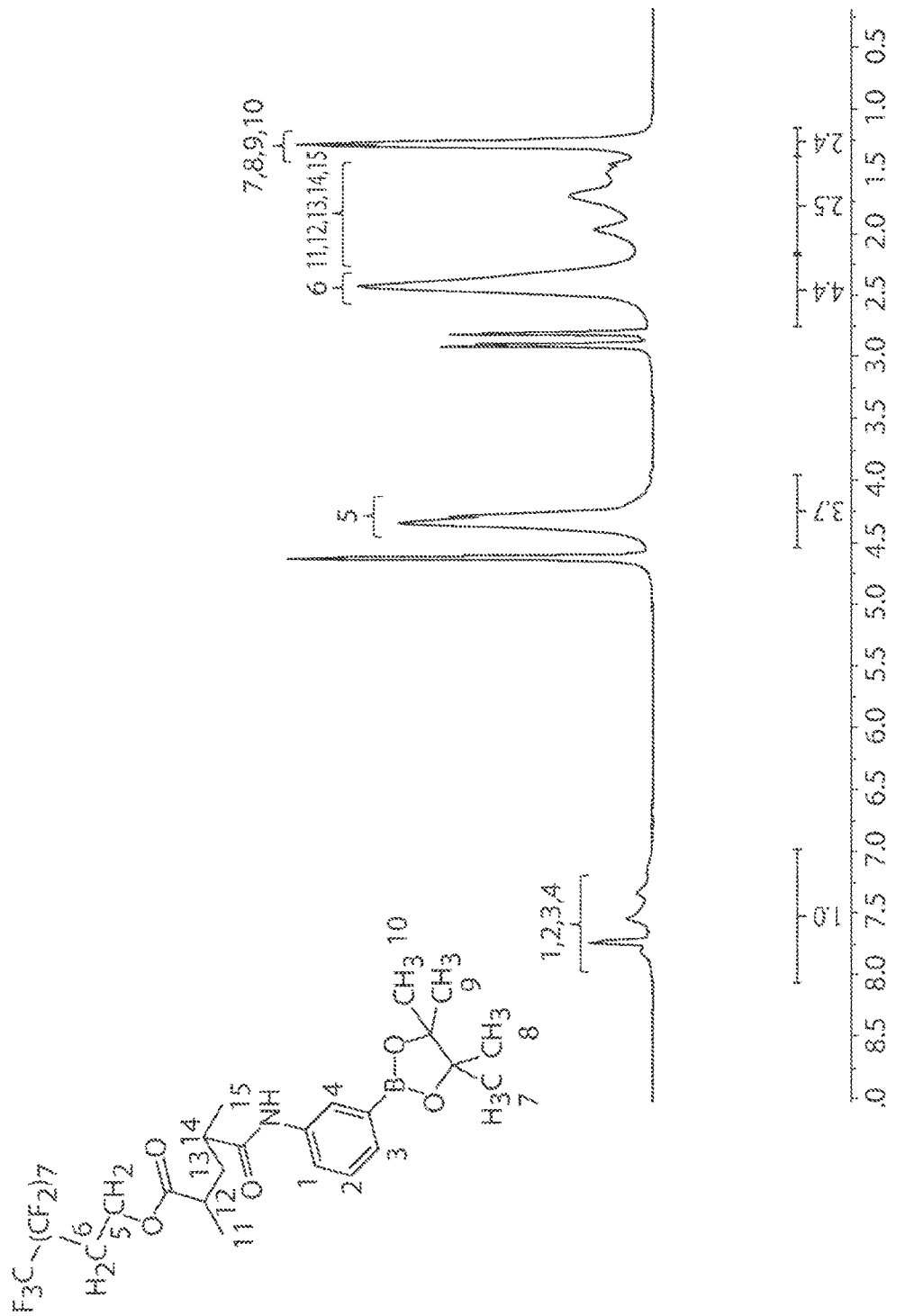
FIGS. 11A-11B illustrate Proton Nuclear Magnetic Resonance ($^1$H-NMR) spectra of certain copolymers, in accordance with another set of embodiments.
Figure 11B:
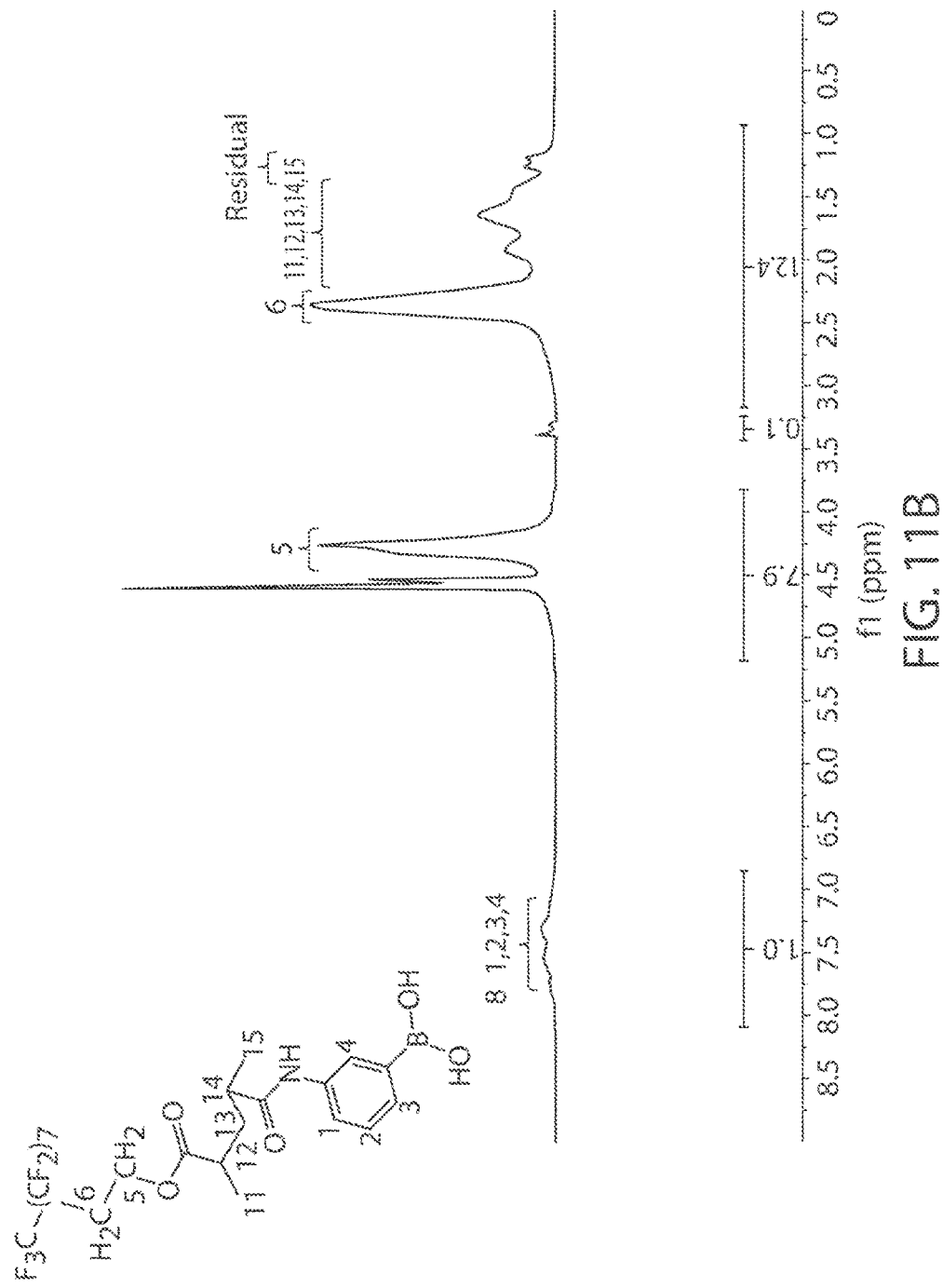

In this example, monomers N-[3-(4,4,5,5-tetramethyl-1,3,2-dioxaborolan-2-yl)phenyl] acrylamide (CAS RN 874363-18-5) and 1H,1H,2H,2H-heptadecafluorodecyl acrylate (CAS 27905-45-9) were dissolved at monomeric ratios of as low as 1:999 up to 1:1 in dimethylformamide (DMF) with azobisisobutyronitrile (AIBN) as the thermal radical initiator at from 0.01 mol % to 30 mol %. The solution was degassed by bubbling nitrogen gas through it, and the reactor was closed and heated at 70° C. with stirring for two days. The solution in some cases turned turbid within about an hour of polymerization. After the polymerization was completed, for example after two days, the polymers were purified by precipitation in an excess of methanol and repeatedly washing the polymer with methanol, followed by drying in vacuum at from 70° C. to 90° C. for hours. The dried polymers represented the protected version of the surfactant copolymer with the boronic acid present as its pinacol ester along the polymer chain. To remove the pinacol and activate the boronic acid and its surfactant functionality, polymers were added to a 1 M solution of hydrochloric acid and stirred overnight at room temperature or elevated temperature under reflux (100° C.). Following deprotection, the polymer was precipitated and washed in excess methanol, followed by drying in vacuum at 70° C. In some embodiments, all boronic acid groups were deprotected (accessible), while in other embodiments not all pinacol protection groups were removed and a partially deprotected copolymer was obtained with both accessible and inaccessible boronic acid side groups along the polymer chain. (FIG. 11A-FIG. 11B). The polymer was used to form water-in-fluorocarbon (e.g., HFE-7500) stable emulsions exactly as the polymers made from 3-acrylamidophenylboronic acid, with polyvinyl alcohol (PVA), dextran, or protein solutions such as fetal bovine serum (FBS) in the aqueous drops.

NOTE 8.1: In contrast to other methods in this disclosure, the approach above in this example uses a protected boronic acid monomer. The protected monomer was more soluble in DMF and may have helped to achieve higher and more homogenous incorporation of the monomer into the polymer chain during copolymer polymerization in DMF. The deprotection of the boronic acid ester in hydrochloric acid (by formation of pinacol) "activated" the polymer for use as a surfactant capable of complexing with the dissolved species, like PVA, in the aqueous phase.

NOTE 8.2: There was a pronounced functional difference between copolymers formed using the unprotected boronic acid monomer (other method in this disclosure) versus those using the protected boronic acid monomers (method above in this example). The use of copolymers from protected boronic acid monomers yielded, after deprotection and emulsion formation, drops that were substantially less adherent ("sticky") than drops stabilized with copolymers from unprotected boronic acids in the initial polymer synthesis. Sticky polymer surfactants were more likely to adhere to microfluidic channel walls and to each other (see example below on adherent drops for additive drop assembly).

NOTE 8.3: The solubility of the polymers in FIFE-7500 depended on the amount of AIBN initiator used during copolymer synthesis. As commonly known by those of ordinary, skill in the art, varying the amount of initiator influences the polymer length may have an influence on copolymer solubility. By tuning the amount of AIBN initiator used in the polymerization, the solubility of the polymer in HFE as well as the strength of the interfacial shell was able to be tuned.

FIG. 11A-FIG. 11B show Proton Nuclear Magnetic Resonance ($^1$H-NMR) spectra of pinacol-protected PFDMA-APBA (boronic ester with pinacol) after polymerization (FIG. 11A) and after removal of the pinacol ("deprotection," FIG. 11B). Numbers above spectra indicate expected protons causing the resonance peaks, corresponding to the chemical structures on the left of the spectra. Numbers below spectra and above axes are relative integration values (area under peaks).

Example 9

Fabrication of Emulsion Drops Using Activated Fluorophilic Protected Boronic Acid Copolymers Water-in-fluorocarbon emulsions were stabilized in this example using the fluorophilic boronic acid copolymers (such as PFDA-APBA, obtained from the monomers 1H,1H,2H,2H-heptadecafluorodecyl acrylate and 3-(acrylamido)phenyl boronic acid) that was obtained by activating (deprotecting) the boronic acid functionality from its pinacol ester protected version (see Example 8 above). The aqueous drops included complexing molecules such as PVA, dextran, or biological molecules such as proteins present in fetal bovine serum (FBS) in water. The fluorinated copolymer solution was prepared by dissolving the fluorophilic boronic acid copolymers at 2 wt % in HFE-7500 and heating the solution for 2 hours at 50° C. in a sealed container. The mixture was then allowed to cool and passed through a syringe filter with 1 micron pores to produce a clear solution used to form emulsions.

Stable emulsion drops were formed in microfluidic drop makers using PVA in water at 5 wt %, 1 wt % and 0.1 wt % and with the fluorinated copolymer in HFE-7500 at 50 mg/mL, using copolymers with 20 mol %, 5 mol %, and 0.5 mol % boronic acid. PVA molecular weights between 10 kg/mol and 100 kg/mol were used.

Example 10

Adherent Drops for Additive Drop Assembly

Drops stabilized with the copolymer PFDA-APBA exhibited a tendency to adhere to surfaces and to each other in this example. This adhesive property allowed for the formation of large secondary structures, like long continuous filaments of aqueous emulsion drops in immiscible fluids such as HFE-7500, as demonstrated in FIG. 12A-FIG. 12B. The production of such and other superstructures may be amenable to 3-D printing and other additive manufacturing and assembly methods, including biological 3-D printing. For example, cells or cell clusters seeded in the aqueous drops may be printed into secondary micro- and macroscopic architectures to spatially guide their proliferation and create cell colonies with desired three-dimensional morphologies.

Figure 12A:
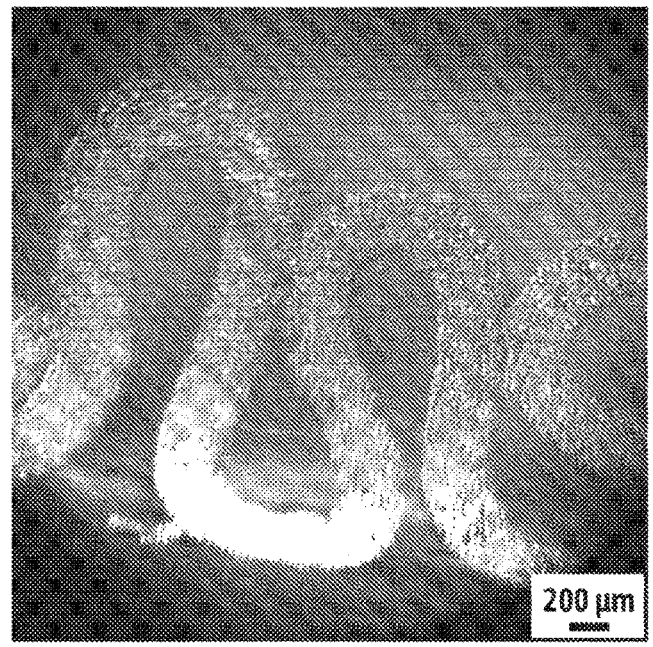
FIGS. 12A-12B illustrate micrographs at different magnifications of filaments obtained from additive drop assembly, in accordance with another set of embodiments.
Figure 12B:
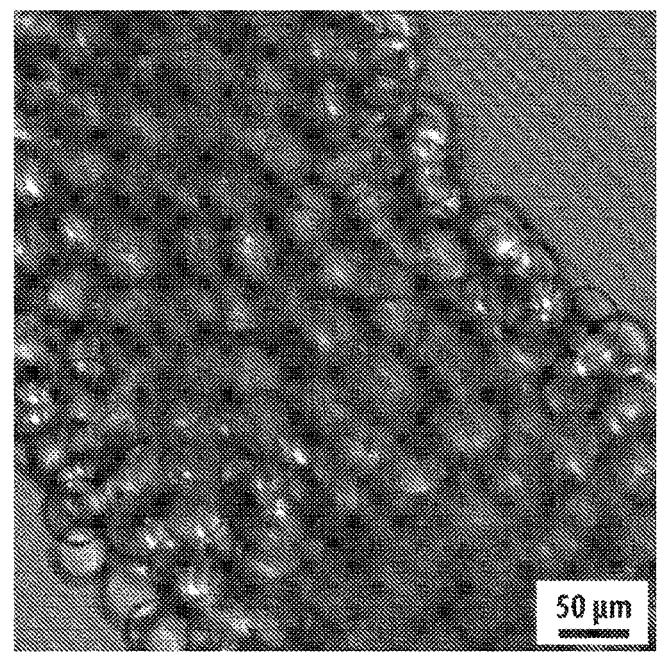

FIG. 12A-FIG. 12B show micrographs at different magnifications of filaments obtained from additive drop assembly using adherent aqueous drops in HFE-7500 that were stabilized and endowed with self-adhesive properties using PFDA-APBA at 3 wt % in the HFE-7500 and 2 wt % PVA inside the aqueous drops.

Example 11

DEXTRAN as Complexing Molecule in Aqueous Drops

Stable emulsion drops were formed in this example in microfluidic drop makers using dextran of from 10 kg/mol to 100 kg/mol in water at from 0.1 wt % to 0.5 wt %, and with the fluorinated copolymer in HFE-7500 at 50 mg/mL, using copolymers with 20 mol % boronic acid. In one embodiment, a dilute concentration of fluorescently labeled dextran was used as the complexing molecule in the aqueous drops to form the interfacial film with the fluorophilic boronic acid copolymers (such as PFDA-APBA). The dyed polymer was observed by fluorescent confocal microscopy to accumulate at the perimeter of the drop, demonstrating film formation at the interface. This accumulation of dextran at the interface was not observed when water-in-fluorocarbon emulsions were studied that did not include airy of the fluorophilic boronic acid copolymers in this disclosure (FIG. 13N).

Figures 13A, 13B, 13C, 13D, 13E:
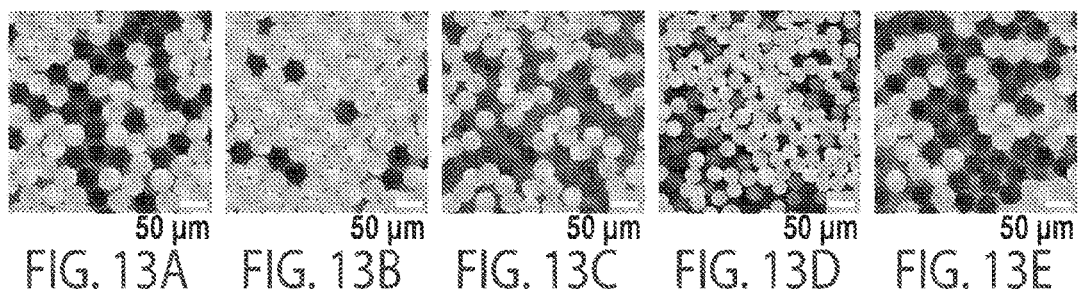
FIGS. 13A-13O illustrate fluorescent confocal microscopy images of fluorescent dyes in water-in-fluorocarbon emulsions, in accordance with another set of embodiments.
Figures 13F, 13G, 13H, 13I, 13J:
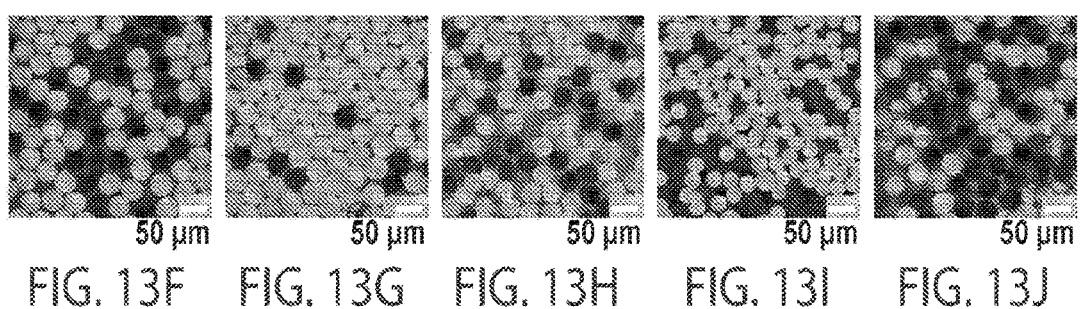
Figures 13K, 13L, 13M, 13N, 13O:
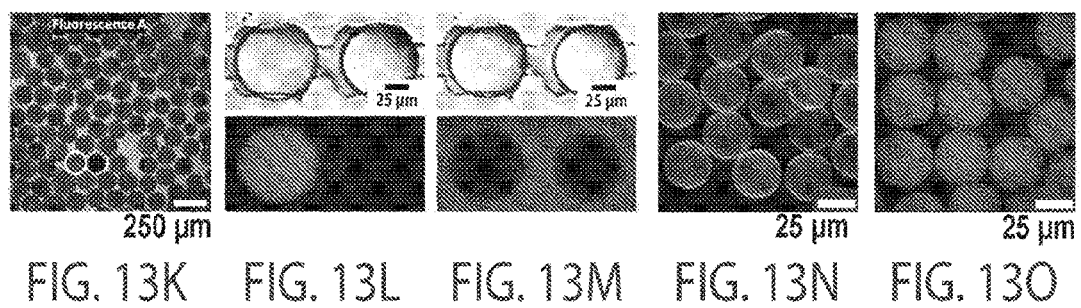

FIG. 13A-FIG. 13O show fluorescent confocal microscopy images of fluorescent dyes in water-in-fluorocarbon emulsions (aqueous drops with complexing molecule in HFE-7500 stabilized with 3 wt % PFDMA-APBA copolymers): FIGS. 13A-13E: Mixture of aqueous drops containing fluorescein sodium salt fluorescent dye and 2 wt % PVA (bright circles) and not containing the dye (dark circles) after: FIG. 13A. 3 hours at 25° C.; FIG. 13B. 48 hours at 25° C.; FIG. 13C. 24 hours at 37° C.; FIG. 13D. 4 days at 37° C.; FIG. 13E. 20 thermocycles between 72° C. and 95° C. (2 mins per temperature per cycle). FIGS. 13F-13J: Mixture of aqueous drops containing Rhodamine 6G fluorescent dye and 2 wt % PVA (bright circles) and not containing the dye (dark circles) after: FIG. 13F. 3 hours at 25° C.; FIG. 13G. 48 hours at 25° C.; FIG. 13H. 24 hours at 37° C.; FIG. 13I. 4 days at 37° C. FIG. 13J. 20 thermocycles between 72° C. and 95° C. (2 mins per temperature per cycle). Mixture of drops containing DNA, EvaGreen™ fluorescent DNA-indicator dye and 2 wt % PVA (solid circle indicates a positive sample drop with increased fluorescence, while dashed circled dye indicated negative control drop with no fluorescence inside). FIGS. 13L-13M: Aqueous drops containing 2 wt % PVA with (left drop) and without (right drop) Rhodamine 6G trapped in a microfluidic device with low volume of HFE-7500 copolymer solution surrounding the drops immediately (FIG. 13L) and 1 hour (FIG. 13M) after trapping. FIGS. 13N-13O: Aqueous drops containing fluorescently labeled dextran in the aqueous drop as complexing molecule that accumulated at the interface with HFE-7500 containing 3 wt % PFDA-APBA (FIG. 13N), as demonstrated by increased fluorescence at the interface, but not for a non-complexing poly(ethylene oxide)-block-poly (hexafluoropropylene oxide)-block-poly(ethylene oxide) ABA triblock terpolymer surfactant (FIG. 13O) from RAN Biotechnologies.

Example 12

Molecular Diffusion and Extraction in Stabilized Emulsions

The diffusion of fluorescent dyes between drops was studied in this example to assess molecular cross-talk and interactions in water-in-fluorocarbon emulsions. Emulsions stabilized with fluorophilic boronic acid copolymers (unprotected PFDMA-APBA or activated protected PFDA-APBA) at 3 wt in FIFE-7500 with two species of aqueous drops, both containing 2 wt % PVA and one containing fluorescein sodium salt, Rhodamine 6G, or EvaGreen™ were monitored under various conditions for various times. Transfer of dyes between drops was not observed at 25° C. for fluorescein sodium salt (FIG. 13A-FIG. 13B) as well as after 1 day at 37° C. (FIG. 13C), and the same for Rhodamine 6G up to 4 days (FIG. 13F, FIG. 13G, FIG. 13H, FIG. 13I). At 37° C. after 4 days, a small but detectable amount of fluorescein sodium salt was observed in the initially "empty" drops that did not contain any dye during emulsion fabrication (FIG. 13D). After 20 thermal cycles between 72° C. and 95° C. (2 mins per temperature per cycle), no diffusion of the two dyes into the initially "empty" drops was observed (FIG. 13E, FIG. 13J). Fluorescent confocal microscopy on the emulsions revealed that Rhodamine 6G and. EvaGreen™ were extracted from drops into the HFE-7500 phase containing PFDA-ABA (FIG. 13F-FIG. 13M)—which, without wishing to be bound by any particular theory, was potentially due to specific interaction (e.g., hydrogen bonding) or charge-complexation of the positively charged dyes with the boronic acid groups of the fluorophilic copolymers—but did not diffuse into initially empty drops. The dye extraction may be able to be eliminated by diluting the surfactant in the fluorocarbon continuous phase.

Example 13

Extraction of Drop Content from Copolymer Stabilized Water-In-Fluorocarbon Emulsions Aqueous solutions with PVA were used to release contents from the aqueous drops of water-in-fluorocarbon emulsions stabilized with PFDA-APBA in HFE-7500 and PVA or FBS as the complexing agent in the aqueous drops in this example. Emulsions drops were collected in a vial and the excess volume of HET-7500 not containing drops was removed. An aqueous solution with 2 wt % PVA was added on top of the emulsion layer. The emulsion was centrifuged at 10,000 g to separate and remove leftover HFE-7500. The resulting contents were transferred to a 65° C. oven for one hour. After the heat treatment, no emulsion drops were observed upon collection.

In some cases, the complexes can be reversed; for example, the pH may be lowered, which may remove the cross-links in the polymer film; in some cases, the complexes can be reversed through the addition of a competing species, for instance, a competing diol such as ethylene glycol, glucose, or catechol, e.g., due to the high chemical reversibility of the boronic ester formation reaction.

Example 14

Additional Post-Fabrication Stabilization of Water-In-Fluorocarbon Emulsions

A fluorophilic boronic acid copolymer surfactant was used to provide additional stability and further provide protection for water-in-fluorocarbon emulsion drops that were initially produced with and stabilized by other non-film-forming surfactants such as poly(ethylene oxide)-Nock-poly(polyhexafluoropropylene oxide) block copolymer surfactants and contained complexing molecules such as PVA in the aqueous drops in this example. This additional provision of protection was of particular benefit in preparation for droplet polymerase chain reaction (PCR). Specifically, aqueous drops containing 1 wt % PVA were emulsified in HFE-7500 containing poly(ethylene oxide)-block-poly (hexafluoropropylene oxide)-block-poly(ethylene oxide) ABA triblock terpolymer surfactant (from RAN biotechnologies) and were collected into a vial of HFE-7500 containing PFDA-APBA at 2 wt %. Drops collected in this manner were stable under PCR thermocycling conditions, they did not coalesce, while drops collected into a vial of pure HFE-7500 or HFE-7500 solutions of the ABA block copolymer surfactants were not stable and partially coalesced during PCR thermocycling. The film-forming fluorophilic boronic acid copolymers at least partially displaced the traditional surfactant at the interface to provide enhanced stability for PCR. The initial fabrication of drops with such common surfactants may facilitate traditional microfluidic drop-manipulations such as picoinjection to be carried out first, which is limited by the elasticity of the interface when using film-forming surfactants as described here, before providing the drops with high stability for PCR or other environments.

Example 15

In-Droplet Reverse-Transcription Polymerase Chain Reaction (RT-PCR) with Water-In Fluorocarbon Emulsion Drops Stabilized by a Fluorophilic Boronic Acid Copolymer-PVA Complex.

This example describes the use of a fluorophilic boronic acid copolymer to stabilize emulsion drops for reverse-transcription polymerase chain reaction (RT-PCR) without coalescence of the drops during thermocycling or inhibiting the RT-PCR. A microfluidic droplet maker was used to make aqueous droplets of 50 micrometer diameter and 200 micrometer diameter in FIFE-7500 fluorinated fluid containing fluorophilic boronic acid copolymer PFDA-APBA (3 wt %). The droplets contained 2 wt % PVA, Titan One Tube RT-PCR Kit (Roche part Cat. No. 11 939 823 001) reagents, and primers to reverse-transcribe and amplify a fragment of the mouse ActB gene. The template was mRNA from mouse cells; the negative control contained no template. The droplets were collected under mineral oil and then incubated for 30 minutes at 50° C. to perform reverse transcription. PCR cycling was performed essentially according to Titan One kit instructions: Denatured template at 94° C. for 2 min; then performed ten cycles of PCR using 94° C. denaturation for 30 seconds, then annealed for 30 seconds at 54° C., then extended at 68° C. for 45 seconds. Then performed 25 cycles using the same denaturation and annealing conditions, but the extension step was elongated by 5 seconds each cycle (e.g., cycle no. 11 had an additional 5 seconds, cycle no. 12 had an additional 10 seconds, cycle no. 13 had an additional 15 seconds, etc.). Then one final extension of 7 min was performed at 68° C.

Figures 14A, 14B:
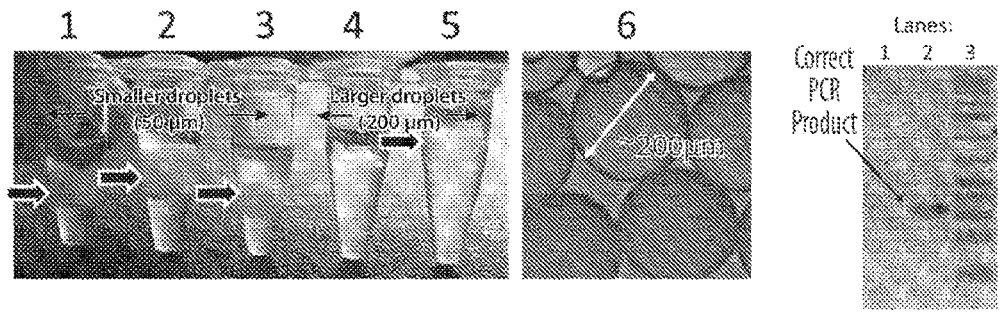
FIG. 14A illustrates photographs of emulsions in polymerase chain reaction (PCR) tubes after reverse-transcription polymerase chain reaction (RT-PCR), and a micrograph of droplets from tube 5 after RT-PCR, in accordance with another set of embodiments.
FIG. 14B illustrates stained agarose gels under ultraviolet (UV) transillumination of droplet content and control samples after RT-PCR, in accordance with another set of embodiments.

After reverse transcription and PCR incubations, reaction tubes were imaged using an Apple iPhone camera (e.g., FIG. 14A). In FIG. 14A, stable droplet emulsions are the arrowed opaque regions between transparent layers of mineral oil (top) and HFE7500 fluid (bottom). Tubes 1-3 contained emulsions comprised of 50 micrometer diameter droplets, while tube 5 emulsion contained droplets of 200 micrometer diameter. In tube 4, the amount of droplets collected was too small to see by eye and not indicated by an arrow. Droplets from tube 5 were removed and imaged by bright field microscopy to create image 6, which shows intact droplets of the expected ~200 micrometers diameter size.

After one-tube reverse transcription and PCR were performed as described above, cycled droplets were run through a DNA purification column according to manufacturer instructions (Zymo part #D4013) and the purified DNA was electrophoresed on a 3% agarose gel and visualized by GelRed staining (Biotium part 41003) and imaged using UV transillumination and digital image capture. The gel (lane 2 in FIG. 14B) demonstrated that the correct PCR product was obtained in the drops stabilized by an interfacial complex of PVA and the fluorophilic boronic acid copolymer PFDA-APBA, demonstrating no detectable interference of the surfactant system with PCR, and high emulsion stability without detectable drop coalescence.

FIG. 14A shows photographs of emulsions in PCR tubes after reverse-transcription polymerase chain reaction (RT-PCR). Tubes 1-3 contained emulsions comprised of 50 micrometer diameter droplets; tubes 4-5 emulsion contained droplets of 200 micrometer diameter. FIG. 14A (image 6) shows a micrograph of the droplets from tube 5 with the unaltered 200 micrometer diameter after RT-PCR. FIG. 14B shows stained agarose gels under UV transillumination of droplet content and control samples after RT-PCR: Lanes: 1. Negative control: RT-PCR in droplets with no RNA template; 2. Sample: RT-PCR in droplets with RNA template; 3. Mixture of 50 base pair and 1 kb DNA ladders. Arrow indicates correct size product (~150 base pairs) in sample lane but not negative control lane.

Example 16

In-Droplet Polymerase Chain Reaction (PCR) with Water-In-Fluorocarbon Emulsion Drops Stabilized by a Fluorophilic Boronic Acid Copolymer-PVA Complex.

Figures 15A, 15B, 15C, 15D:
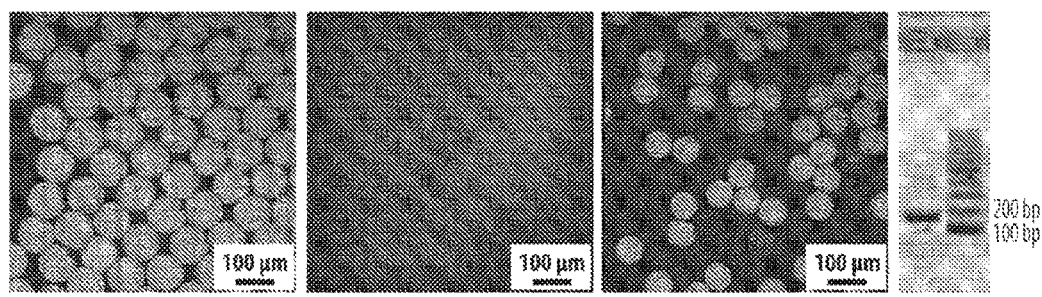
FIGS. 15A-15C illustrate fluorescent micrographs of positive and negative PCR sample droplets, in accordance with another set of embodiments.
FIG. 15D illustrates an agarose gel after electrophoresis, in accordance with another set of embodiments.

This example describes the use of the fluorophilic boronic acid copolymer to stabilize emulsion drops for polymerase chain reaction (PCR) without coalescence of the drops during thermocycling or inhibiting the PCR, demonstrated by the successful PCR amplification using a Taqman™ probe. A microfluidic dropmaker was used to generate 150 micron diameter water-in-fluorocarbon drops. Positive Sample droplets contained 2 wt % PVA, ix PrimeTime® Gene Expression Master Mix (IDT catalog #1055770), Ix mouse ActB PCR primers and probe (Forward primer sequence GACTCATCGTACTCCTGCTTG, reverse primer sequence GATTACTGCTCTGGCTCCTAG, fluorescent probe sequence CTGGCCTCACTGTCCACCTTCC, IDT catalog #Mm.PT.39a.22214843.g), 0.5% PVA, and ActB DNA template (~1 nanogram/microliters). Negative Control droplets lacked ActB DNA template, but were otherwise identical to Positive Sample Droplets. The continuous phase was HFE-7500 with fluorophilic boronic acid copolymer PFDA-APBA (at 3 wt %). Prior to PCR thermal cycling, a mixed-droplet sample was created by combining some Positive Sample droplets with some Negative Control droplets. To prevent evaporation, droplets were overlaid with mineral oil prior to cycling. Thermal cycling conditions: 95° C. for 3 min, then 35 cycles of 95° C. 10 sec, 54° C. 15 sec, extended 72° C. for 30 sec; then held 4° C. After cycling, a fraction of each droplet sample was added to a disposable hemocytometer (Bulldog Bio cat #DHC-N420-4) and imaged using fluorescence microscopy. Positive Sample droplets were brightly fluorescent, while the Negative Control droplet fluorescence was barely detectable (e.g., FIG. 15A and FIG. 15B, respectively). A mixed-droplet sample image shows a mix of fluorescent and non-fluorescent droplets, indicating the successful PCR amplification in the Positive Sample Droplets (FIG. 15C). To confirm the PCR generated the appropriate 147 base pair product, cycled Positive Control droplets were run through a DNA purification column according to manufacturer instructions (Zymo part #D4013) and the purified DNA was electrophoresed on a 3% agarose gel and visualized by GelRed staining and UV illumination. The product size was ~150 bp (FIG. 15D (left lane)), as determined by comparison to the bottom two bands of the 100 base pair ladder (FIG. 15D (right lane)).

FIG. 15A-FIG. 15C show fluorescent micrographs of positive and negative PCR sample droplets. FIG. 15A shows that Positive Sample droplets containing the Taqman™ probe were brightly fluorescent after PCR. FIG. 15B illustrates that the Negative Control droplets showed barely detectable fluorescence. FIG. 15C illustrates that a mixed-droplet sample of Positive Sample and Negative Control droplets showed a mix of fluorescent and non-fluorescent droplets. FIG. 15D (left lane, right lane) shows an agarose gel after electrophoresis showing the correct PCR product for the Positive Sample droplets (FIG. 15D, left lane) as compared to the DNA ladder (FIG. 15D, right lane).

Example 17

Mammalian Cell Expansion in Aqueous Droplets Stabilized with the PVA-Fluorinated Boronic Acid System Growth of mammalian cells in cell culture dishes and flasks generally requires that the cell concentration is kept below one million cells per milliliter, at least to ensure that cells have sufficient nutrients and to prevent rapid accumulation of undesired cell metabolism by-products. Mammalian cell growth is thus generally challenging in microfluidic droplets: One cell in a 500 picoliter (pL) droplet is at a relatively high effective concentration of two million cells per mL, and droplets stabilized by commercially available surfactants (e.g., 008-FluoroSurfactant, RAN Biotechnologies, USA) are often unstable towards coalescence and merge during incubation. In some embodiments of the instant disclosure, K-562 cells (derived from human lymphoid cells, part CCL-243™, ATCC®, USA) were used, which cells have a doubling time of between 18 and 24 hours, to demonstrate that mammalian cells remained viable and were able to expand in number in large droplets (~33 nL volume) formed with the PVA-fluorinated boronic acid system (0.5 wt % PVA in aqueous drops and 3 wt % PFDA-APBA in HFE-7500). K-562 cells, cultured under standard conditions, were stained with CellTracker™ green (ThermoFisher Catalog number C7025) for 30 min at 37° C. and then pelleted by centrifugation (1000× gravity for 90 seconds). Cells were re-suspended to a final concentration of ~30,000 cells/mL in cell culture medium supplemented with 10% FBS and 1% Penicillin-Streptomycin Solution (ATCC catalog numbers 30-2005, 30-2020 30-2300, respectively) containing 16% OptiPrep (Sigma-Aldrich-D1556), and 0.5 wt % PVA. A microfluidic dropmaker was used to encapsulate this cell solution into (~33 nL droplets in continuous phase HFE-7500 containing fluorinated boronic acid. At this input cell concentration and droplet size, almost all droplets contained either one or zero cells. Droplets were collected in a monolayer in 48-well cell culture plates, overlaid with cell culture medium, and placed in a cell culture incubator to facilitate cell growth. Cells were imaged by fluorescence confocal microscopy at time zero and after 48 h and 96 h incubation in a 37° C. cell culture incubator. Immediately after droplet making (time zero), most droplets contained one or zero very bright cells (see representative image in FIG. 16A). Actively growing K-562 cells expanded in number after 48 h and 96 h incubation (see images in FIG. 16B and FIG. 16C, respectively). The fluorescence intensity of individual cells decreased with each division, due to dilution of the CellTracker™ green stain into daughter cells. These data suggest that one cell in a 33 nL droplet (an effective concentration of 30,000 cells per mL) was able to undergo several cell divisions during 96 h incubation at 37° C.

FIG. 16A-FIG. 16C are confocal microscopy images of mammalian K562 cells expanding in water-in-fluorocarbon drops stabilized with PFDA-APBA in HFE-7500 and PVA in the aqueous cell solution: FIG. 16A shows a single cell in 33 nL water drop after drop fabrication. FIG. 16B shows expanded cells in single drop after 48 hours, and FIG. 16C shows after 96 hours incubation at 37° C.

Example 18

Oil-In-Water Emulsion Stabilization

Complexation of hydrophilic polyols with lipophilic (for example PHA-APBA) or fluorophilic (for example PFDA-APBA) boronic acid copolymers in this disclosure was also able to stabilize hydrocarbon-in-water or fluorocarbon-in-water emulsions. These emulsions were inverted as compared to the other examples, with water having been the continuous phase and oil drops (fluoro- or hydrocarbon) having been the dispersed phase. The interfacial film formed in these inverted emulsions also stabilized the droplets from coalescence, which was uncommon for single-molecules surfactant systems. Fluorocarbon-in-water drops of sizes with interfacial film stabilization were obtained by using blunt syringe needles and injecting a solution of 3 wt % PFDMA-APBA into a resting aqueous solution of 2 wt % PVA in DMEM, as shown in FIG. 17A-FIG. 17C. Drops produced were from 1.5 mm to 3 mm in diameter and did not coalesce when in contact.

FIG. 17A-FIG. 17C show optical microscopy images of millimeter sized fluorocarbon-in-water emulsion drop formation (FIG. 17A and FIG. 17B) and fabricated drop (FIG. 17C) using a blunt needle as drop formation nozzle. The dispersed fluid was HFE-7500 with 3 wt % PFDMA-APBA and the continuous media was 2 wt % PVA dissolved in Dulbecco's Modified Eagle Medium (DMEM).

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

When the word "about" is used herein in reference to a number, it should be understood that still another embodiment of the invention includes that number not modified by the presence of the word "about."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A composition, comprising:
   an oil droplet encapsulated within a polymer film contained within an aqueous fluid, wherein the polymer film comprises a complex of a random amphiphilic copolymer and a hydrophilic complexing molecule;
   wherein the random amphiphilic copolymer comprises poly (hexylacrylate-co-3-(acrylamido) phenylboronic acid) (PHA-APBA).

2. The composition of claim 1, wherein the random amphiphilic copolymer is present in the oil droplet.

3. The composition of claim 1, wherein the oil droplet comprises a hydrocarbon.

4. The composition of claim 1, wherein the oil droplet comprises a fluorocarbon.

5. The composition of claim 1, wherein the hydrophilic complexing molecule comprises a hydrophilic polyol.

6. The composition of claim 1, wherein the hydrophilic complexing molecule comprises polyvinyl alcohol (PVA).

7. The composition of claim 1, wherein the aqueous fluid comprises Dulbecco's Modified Eagle Medium (DMEM).

8. The composition of claim 1, wherein the oil droplet has an average diameter of less than 1 cm.

9. The composition of claim 1, wherein the hydrophilic complexing molecule comprises a polysaccharide.

10. The composition of claim 1, wherein the hydrophilic complexing molecule comprises iodixanol.

11. The composition of claim 1, wherein the hydrophilic complexing molecule is present in the aqueous fluid.

12. The composition of claim 1, wherein the oil droplet comprises a fluorinated oil.

13. The composition of claim 12, wherein the fluorinated oil comprises methoxyperfluorobutane.

14. The composition of claim 1, wherein the oil droplet has an average diameter of less than 1 mm.

* * * * *